(12) United States Patent
Laghi et al.

(10) Patent No.: US 10,907,210 B2
(45) Date of Patent: Feb. 2, 2021

(54) DIFFERENT LEVELS IN BLOOD CELL SAMPLES OF EMT-MARKERS FOR THE DIAGNOSIS OF CANCER, IN PARTICULAR OF COLORECTAL (CRC) AND PANCREATIC (PC) CANCER

(71) Applicant: HUMANITAS MIRASOLE S.P.A., Rozzano (IT)

(72) Inventors: Luigi Laghi, Rozzano (IT); Giuseppe Celesti, Rozzano (IT)

(73) Assignee: HUMANITAS MIRASOLE S.P.A., Rozzano (IT)

( * ) Notice: Subject to any disclaimer, the term of this patent is extended or adjusted under 35 U.S.C. 154(b) by 0 days.

(21) Appl. No.: 15/104,129

(22) PCT Filed: Dec. 16, 2014

(86) PCT No.: PCT/EP2014/078095
§ 371 (c)(1),
(2) Date: Jun. 13, 2016

(87) PCT Pub. No.: WO2015/091575
PCT Pub. Date: Jun. 25, 2015

(65) Prior Publication Data
US 2016/0312296 A1 Oct. 27, 2016

(30) Foreign Application Priority Data

Dec. 16, 2013 (EP) .................................. 13197367

(51) Int. Cl.
*C12Q 1/6886* (2018.01)

(52) U.S. Cl.
CPC ..... *C12Q 1/6886* (2013.01); *C12Q 2600/158* (2013.01)

(58) Field of Classification Search
CPC ............ C12Q 1/6886; C12Q 2600/158; C12Q 1/6851; C12Q 2600/112
See application file for complete search history.

(56) References Cited

FOREIGN PATENT DOCUMENTS

| EP | 1813681 A2 | 8/2007 |
|---|---|---|
| WO | 2008029290 A2 | 3/2008 |
| WO | 2012103025 A2 | 8/2012 |
| WO | 2012149014 A1 | 11/2012 |

OTHER PUBLICATIONS

Markou et al. Clinical Chemistry. 2011. 57(3):421-430.*
Ramskold et al. Nat Biotechnol. 2012. 30(8):777-782.*
Chen et al. The Prostate. 2013. 73:813-826.*
Celesti. "Mesenchymal features mediated by Twist1 in Colorectal cancer cells and microenvironment". Doctoral Thesis. 2011.*
Cohen et al. Clinical Colorectal Cancer. 2006. (6)2:125-132. (Year: 2006).*
Bates et al. Cancer Biology & Therapy. 2005. 4:4, 365-370. (Year: 2005).*
Celesti et al., "Presence of Twist1-Positive Neoplastic Cells in the Stroma of Chromosome-Unstable Colorectal Tumors", Gastroenterology, 2013, vol. 145, No. 3, pp. 647-657.
Larriba et al., "Snail2 cooperates with Snail in the repression of vitamin D receptor in colon cancer," Carcinogenesis, 2009, vol. 30, No. 8, pp. 1459-1468.
Ohuchida et al., "Twist, a novel oncogene, is upregulated in pancreatic cancer: Clinical implication of Twist expression in pancreatic juice", International Journal of Cancer, 2007, vol. 120, No. 8, pp. 1634-1640.
Pham et al., "Loss of 15-Hydroxyprostaglandin Dehydrogenase Increases Prostaglandin E2 in Pancreatic Tumors", Pancreas, 2010, vol. 39, No. 3, pp. 332-339.
Imamichi et al., "Colllagen type I-induced Smad-interacting protein 1 expression downregulates E-cadherin in pancreatic cancer", Oncogene, 2006, vol. 26, No. 16, pp. 2381-2385.
Fan et al., Snail promotes lymph node metastasis and Twist enhances tumor deposit formation through epithelial-mesenchymal transition in colorectal cancer, Human Pathology, 2013, vol. 44, No. 2, pp. 173-180.
International Search Report and Written Opinion for International Application No. PCT/EP2014/078095, ( 22 Pages)( dated Jun. 29, 2015).

* cited by examiner

*Primary Examiner* — Joseph G. Dauner
(74) *Attorney, Agent, or Firm* — Lucas & Mercanti, LLP

(57) ABSTRACT

The present invention concerns a method for determining if a subject is affected by a colorectal or pancreatic cancer or for determining the stage and/or the progression of a colorectal cancer. By measuring the presence of a panel of m RNAs encoding for transcription factors/genes involved in epithelial to mesenchymal transition in a blood sample, wherein different mRNA levels of a set of genes comprising TWIST1, SLUG, ZEB2, ZEB1 and CDH1, are indicative of colorectal cancer or pancreatic cancer diagnosis, and/or of colorectal cancer stage at diagnosis, and/or of CRC metastatic progression after surgery. The invention concerns also the use of kits to work the method.

5 Claims, 12 Drawing Sheets

Figure 1:
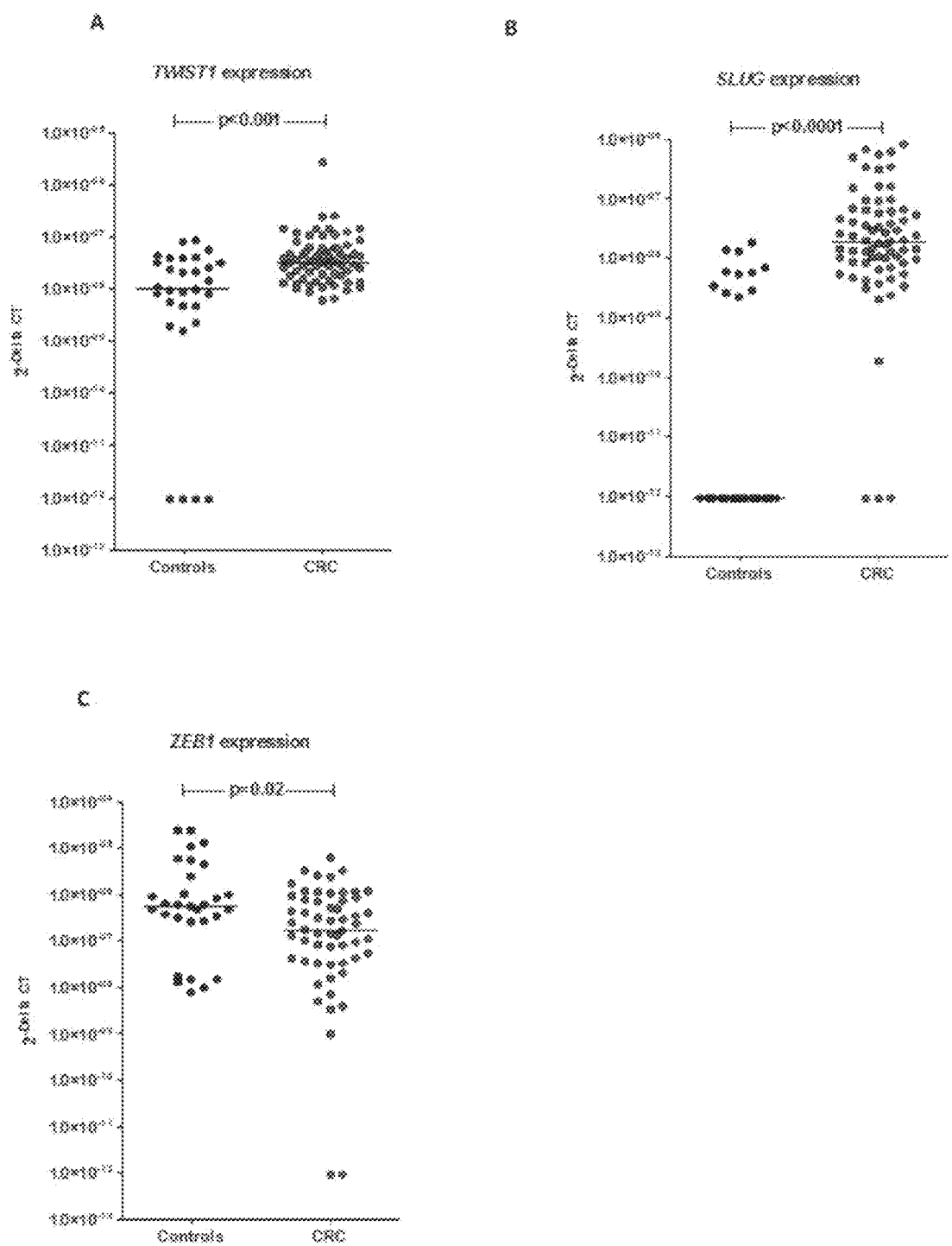

Specification includes a Sequence Listing.

SLUG

TWIST1

SEQUENCE LISTING

<160> NUMBER OF SEQ ID NOS: 27

<210> SEQ ID NO 1
<211> LENGTH: 1669
<212> TYPE: DNA
<213> ORGANISM: Homo sapiens

<400> SEQUENCE: 1

```
gaggtataag agcctccaag tctgcagctc tcgcccaact cccagacacc tcgcgggctc      60
tgcagcaccg gcaccgtttc caggaggcct ggcggggtgt gcgtccagcc gttgggcgct     120 ttcttttttgg acctcggggc catccacacc gtccctccc cctccgcct ccctccccgc      180 ctcccccgcg cgccctcccc gcggaggtcc ctcccgtccg tcctcctgct ctctcctccg     240
cgggccgcat cgcccgggcc ggcgccgcgc gcggggggaag ctggcgggct gaggcgcccc    300
gctcttctcc tctgccccgg gcccgcgagg ccacgcgtcg ccgctcgaga gatgatgcag     360
gacgtgtcca gctcgccagt ctcgccggcc gacgacagcc tgagcaacag cgaggaagag     420
ccagaccggc agcagccgcc gagcggcaag cgcggggggac gcaagcggcg cagcagcagg     480
cgcagcgcgg gcgcggcgc ggggcccggc ggagccgcgg gtggggcgt cggaggcggc      540 gacgagccgg gcagcccggc ccagggcaag cgcggcaaga agtctgcggg ctgtggcggc     600
ggcggcggcg cgggcggcgg cggcggcagc agcagcggcg gcgggagtcc gcagtcttac     660
gaggagctgc agacgcagcg ggtcatggcc aacgtgcggg agcgccagcg cacccagtcg     720
ctgaacgagg cgttcgccgc gctgcggaag atcatcccca cgctgccctc ggacaagctg     780
agcaagattc agaccctcaa gctggcggcc aggtacatcg acttcctcta ccaggtcctc     840
cagagcgacg agctggactc caagatggca agctgcagct atgtggctca cgagcggctc     900
agctacgcct tctcggtctg gaggatggag ggggcctggt ccatgtccgc gtcccactag     960
caggcggagc cccccacccc ctcagcaggg ccggagacct agatgtcatt gtttccagag    1020
aaggagaaaa tggacagtct agagactctg gagctggata actaaaaata aaaatatatg    1080
ccaaagattt tcttggaaat tagaagagca aaatccaaat tcaaagaaac agggcgtggg    1140
gcgcactttt aaaagagaaa gcgagacagg cccgtggaca gtgattccca gacgggcagc    1200
```

-continued

| | |
|---|---|
| ggcaccatcc tcacacctct gcattctgat agaagtctga acagttgttt gtgtttttt | 1260 |
| tttttttttt tttgacgaag aatgttttta ttttattt tttcatgcat gcattctcaa | 1320 |
| gaggtcgtgc caatcagcca ctgaaaggaa aggcatcact atggactttc tctattttaa | 1380 |
| aatggtaaca atcagaggaa ctataagaac acctttagaa ataaaaatac tgggatcaaa | 1440 |
| ctggcctgca aaaccatagt cagttaattc ttttttttcat ccttcctctg aggggaaaaa | 1500 |
| caaaaaaaaa cttaaaatac aaaaaacaac attctattta tttattgagg acccatggta | 1560 |
| aaatgcaaat agatccggtg tctaaatgca ttcatatttt tatgattgtt ttgtaaatat | 1620 |
| ctttgtatat ttttctgcaa taaataaata taaaaatt agagaaaaa | 1669 |

<210> SEQ ID NO 2
<211> LENGTH: 2112
<212> TYPE: DNA
<213> ORGANISM: Homo sapiens

<400> SEQUENCE: 2

| | |
|---|---|
| aaaacgggct cagttcgtaa aggagccggg tgacttcaga ggcgccggcc cgtccgtctg | 60 |
| ccgcacctga gcacggcccc tgcccgagcc tggcccgccg cgatgctgta gggaccgccg | 120 |
| tgtcctcccg ccggaccgtt atccgcgccg ggcgcccgcc agaccccgctg gcaagatgcc | 180 |
| gcgctccttc ctggtcaaga agcatttcaa cgcctccaaa aagccaaact acagcgaact | 240 |
| ggacacacat acagtgatta tttccccgta tctctatgag agttactcca tgcctgtcat | 300 |
| accacaacca gagatcctca gctcaggagc atacagcccc atcactgtgt ggactaccgc | 360 |
| tgctccattc cacgcccagc tacccaatgg cctctctcct ctttccggat actcctcatc | 420 |
| tttggggcga gtgagtcccc ctcctccatc tgacacctcc tccaaggacc acagtggctc | 480 |
| agaaagcccc attagtgatg aagaggaaag actacagtcc aagctttcag accccccatgc | 540 |
| cattgaagct gaaaagtttc agtgcaattt atgcaataag acctattcaa cttttttctgg | 600 |
| gctggccaaa cataagcagc tgcactgcga tgcccagtct agaaaatctt tcagctgtaa | 660 |
| atactgtgac aaggaatatg tgagcctggg cgccctgaag atgcatattc ggacccacac | 720 |
| attaccttgt gtttgcaaga tctgcggcaa ggcgttttcc agaccctggt tgcttcaagg | 780 |
| acacattaga actcacacgg gggagaagcc ttttctcttgc cctcactgca acagagcatt | 840 |
| tgcagacagg tcaaatctga gggctcatct gcagacccat tctgatgtaa agaaatacca | 900 |
| gtgcaaaaac tgctccaaaa ccttctccag aatgtctctc ctgcacaaac atgaggaatc | 960 |
| tggctgctgt gtagcacact gagtgacgca atcaatgttt actcgaacag aatgcatttc | 1020 |
| ttcactccga agccaaatga caaataaagt ccaaggcat tttctcctgt gctgaccaac | 1080 |
| caaataatat gtatagacac acacacatat gcacacacac acacacacac ccacagagag | 1140 |
| agagctgcaa gagcatggaa ttcatgtgtt taaagataat cctttccatg tgaagtttaa | 1200 |
| aattactata tatttgctga tggctagatt gagagaataa aagacagtaa cctttctctt | 1260 |
| caaagataaa atgaaaagca cattgcatct tttcttccta aaaaaatgca agatttaca | 1320 |
| ttgctgccaa atcatttcaa ctgaaaagaa cagtattgct ttgtaataga gtctgtaata | 1380 |
| ggatttccca taggaagaga tctgccagac gcgaactcag gtgccttaaa aagtattcca | 1440 |
| agtttactcc attcatgtc ggttgtctgg ttgccattgt tgaactaaag ccttttttttg | 1500 |
| attacctgta gtgctttaaa gtatattttt aaagggagg aaaaaaataa caagaacaaa | 1560 |
| acacaggaga atgtattaaa agtattttg ttttgttttg ttttttgccaa ttaacagtat | 1620 |
| gtgccttggg ggaggaggga aagattagct ttgaacattc ctggcgcatg ctccattgtc | 1680 |

| | | |
|---|---|---|
| ttactatttt aaaacatttt aataatttt gaaaattaat taaagatggg aataagtgca | 1740 | |
| aaagaggatt cttacaaatt cattaatgta cttaaactat ttcaaatgca taccacaaat | 1800 | |
| gcaataatac aataccccctt ccaagtgcct ttttaaattg tatagttgat gagtcaatgt | 1860 | |
| aaatttgtgt ttattttat atgattgaat gagttctgta tgaaactgag atgttgtcta | 1920 | |
| tagctatgtc tataaacaac ctgaagactt gtgaaatcaa tgtttctttt ttaaaaaaca | 1980 | |
| atttcaagt tttttttaca ataaacagtt ttgatttaaa atctcgtttg tatactattt | 2040 | |
| tcagagactt tacttgcttc atgattagta ccaaaccact gtacaaagaa ttgtttgtta | 2100 | |
| acaagaaaaa aa | 2112 | |

<210> SEQ ID NO 3
<211> LENGTH: 9243
<212> TYPE: DNA
<213> ORGANISM: Homo sapiens

<400> SEQUENCE: 3

| | | |
|---|---|---|
| atttcatttc ttccactaaa gcgtttgcgg agacttcaag gtataatcta tcccagatcc | 60 | |
| tttcccagag agaaacttgg cgatcacgtt ttcacatgat gctcacgctc agggcgcttc | 120 | |
| aattatccct ccccacaaag ataggtggcg cgtgtttcag ggtctctcgt ctctctccta | 180 | |
| cagaaaagaa aaagaaaaaa atgtcattag aagaggcgta acacgtcagt ccgtccccag | 240 | |
| gtttgtgttt cctggagtgg ccgaaagaga tcagttctaa cctgctctgc aggaataacg | 300 | |
| gtcctgcctc ccgacactct tggcgaggtt tttgtacagt ttgctccggg agctgtttct | 360 | |
| tcgcttccac ctttttctcc cccacacttc gcggcttctt catgcttttt cttctcacca | 420 | |
| tttctggcca aaactacaaa caagacttcg cagatcgagc ctgcgtgctg ccgaagcagg | 480 | |
| gcgccgagtc catgcgaact gccatctgat ccgctcttat caatgaagca gccgatcatg | 540 | |
| gcggatggcc cccggtgcaa gaggcgcaaa caagccaatc ccaggaggaa aaacgtggtg | 600 | |
| aactatgaca atgtagtgga cacaggttct gaaacagatg aggaagacaa gcttcatatt | 660 | |
| gctgaggatg acggtattgc caaccctctg gaccaggaga cgagtccagc tagtgtgccc | 720 | |
| aaccatgagt cctccccaca cgtgagccaa gctctgttgc caagagagga agaggaagat | 780 | |
| gaaataaggg agggtggagt ggaacacccc tggcacaaca acgagattct acaagcctct | 840 | |
| gtagatggtc cagaagaaat gaaggaagac tatgacacta tggggccaga agccacgatc | 900 | |
| cagaccgcaa ttaacaatgg tacagtgaag aatgcaaatt gcacatcaga ttttgaggaa | 960 | |
| tactttgcca aaagaaaact ggaggaacgc gatggtcatg cagtcagcat cgaggagtac | 1020 | |
| cttcagcgca gtgacacagc cattatttac ccagaagccc ctgaggagct gtctcgcctt | 1080 | |
| ggcacgccag aggccaatgg caagaagaa atgacctgc cacctggaac tccagatgct | 1140 | |
| tttgcccaac tgctgacctg cccctactgc gaccggggct acaagcgctt gacatcactg | 1200 | |
| aaggagcaca tcaagtaccg ccacgagaag aatgaagaga cttttcctg ccctctctgt | 1260 | |
| agctacacgt ttgcctaccg cacccagctc gagcggcata tggtgacaca caagccaggg | 1320 | |
| acagatcagc accaaatgct aacccaagga gcaggtaatc gcaagttcaa atgcacagag | 1380 | |
| tgtggcaagg ccttcaaata taaacaccat ctgaaagaac acctgcgaat tcacagtggt | 1440 | |
| gaaaaacctt acgagtgccc aaactgcaag aaacgtttct cccattctgg ttcctacagt | 1500 | |
| tcgcacatca gcagcaagaa atgtattggt ttaatctctg taaatggccg aatgagaaac | 1560 | |
| aatatcaaga cggggttcttc ccctaattct gtttcttctt ctcctactaa ttcagccatt | 1620 | |

-continued

```
acccagttaa gaaacaagtt ggagaatgga aaaccactta gtatgtctga acagacaggc    1680
ttacttaaaa ttaaaacaga accactagac ttcaatgact ataaagttct tatggctaca    1740
cacgggttta gtggcactag tcccttatg aatggtgggc ttggagccac cagccctta     1800 ggagttcatc catctgctca gagtccaatg cagcacttag gtgtagggat ggaagcccct    1860
ttacttgggt ttcccaccat gaatagtaat ttaagtgagg tacaaaaggt tctacagatt    1920
gtggacaata ctgttccag gcaaaaaatg gactgcaagg ctgaagaaat ttcaaagttg     1980
aaaggttatc acatgaagga tccatgctct caacctgagg aacaaggagt tacttctcct    2040
aatattccgc ctgtcggtct tccggtagtg agtcataatg gtgccactaa agtattatt     2100 gactatacgt tggaaaaagt caatgaagcc aaagcttgcc tccagagctt gactactgac    2160
tcaaggagac agatcagtaa tataaagaaa gagaagctac gtactttaat agatttggtc    2220
actgatgaca aaatgattga gaaccacaac atatccactc cattttcatg ccagttctgt    2280
aaagaaagtt ttcctggccc catcccttg catcagcatg aacgttacct ttgtaagatg     2340
aatgaagaga tcaaggcggt cctgcagcct catgaaaaca tagtccccaa caaagccgga    2400
gtttttgttg ataataaagc cctcctcttg tcatctgtac tttctgagaa aggaatgaca    2460
agccccatca acccatacaa ggaccacatg tctgtactca agcatacta tgctatgaac     2520 atggagccca actccgatga actgctgaaa atttccattg ctgtgggcct tcctcaggaa    2580
tttgtgaagg aatggtttga acaacgaaaa gtctaccagt actcaaattc caggtcccca    2640
tccctggaaa gaagctccaa gccgttagct cccaacagta accctccac aaaagactct     2700 ttattaccca ggtctcctgt aaaacctatg gactccataa catcaccatc tatagcagaa    2760
ctccacaaca gtgttacgaa ttgtgatcct cctctcaggc taacaaaacc ttcccatttt    2820
accaatatta aaccagttga aaaattggac cactccagga gtaatactcc ttctcccta    2880 aatcttcct ccacatcttc taaaaactcc cacagtagtt catacactcc aaacagcttc    2940
tcttctgagg agctccaggc tgagccttta gacttgtcat taccaaaaca aatgaaagaa    3000
cccaaaagta ttatagccac aaagaacaaa acaaaagcta gtagcatcag tttagatcat    3060
aacagtgttt cttcctcatc tgaaaactca gatgagcctc tgaacttgac ttttatcaag    3120
aaggaatttt caaattcaaa taatctggac aacaaaagca ctaacccagt gttcagcatg    3180 aacccatta gtgccaaacc tttatacaca gctcttccac ctcaaagcgc atttccccct     3240
gctactttca tgccaccagt ccagaccagt attcctgggc tacgaccata cccaggactg    3300
gatcagatga gcttcctacc acatatggcc tacacctacc caactggagc agctactttt    3360
gctgatatgc agcaaaggag aaagtaccag cggaaacaag gatttcaggg agaattgctt    3420
gatggagcac aagactacat gtcaggccta atgatatga cagactccga ctcctgtctg     3480
tctcgcaaaa agatcaagaa gacagagagt ggcatgtatg catgtgactt atgtgacaag    3540
acattccaga aaagcagttc ccttctgcga cataaatacg aacacacagg aaaaagacca    3600
catcagtgtc agatttgtaa gaaagcgttt aaacacaagc accaccttat cgagcactca    3660
aggcttcact cgggcgagaa gccctatcag tgtgataaat gtggcaagcg cttctcacac    3720
tcgggctcgt actcgcagca catgaatcac aggtattcct actgcaagcg ggaggcggag    3780
gagcgggaag cggcggagcg cgaggcgcgc gagaaagggc acttggaacc caccgagctg    3840
ctgatgaacc gggcttactt gcagagcatt acccctcagg ggtactctga ctcggaggag    3900
agggagagta tgccgaggga tggcgagagc gagaaggagc acgagaaaga aggcgaggat    3960
ggctacggga agctgggcag acaggatggc gacgaggagt tcgaggagga agaggaagaa    4020
```

```
agtgaaaata aaagtatgga tacggatccc gaaacgatac gagatgaaga agagactgga    4080
gatcactcca tggacgatag ttcggaggat gggaaaatgg aaaccaaatc agaccacgag    4140
gaagacaata tggaagatgg catgtaataa actactgcat tttaagcttc ctattttttt    4200
ttccagtagt attgttacct gcttgaaaac actgctgtgt taagctgttc atgcacgtgc    4260
ctgacgcttc caggaagctg tagagaggga cagaaggggc ggttcagcca agacagatgt    4320
agacggagtt ggagctgggt attgttaaaa actgcattat gcaaaaattt tgtacagtgt    4380
taaggcctaa aaactgtgtg gttcagagac taattcctgt gtttaatagc atttatactt    4440
taagcacaac tagaaaattg taagaattgc actctactta tgtatcacta caaactttaa    4500
aaaactatgt ctaatttata ttaatacatt ttaaaaaggt gcccgcacta ccatacatca    4560 gtattttat tattattatt gttattcctt tttaatttaa tgtgctcgca ctacaatgca    4620
tcagtattat gattcctctg tactttcctt tcgctattca tcaatttccc atttttttt    4680 tcagcttaag taaccacaca attttaggcc tcaattttt tttttttctg tgaaggaact    4740
tgaagtgatg catgtgtgaa tttaagatac cgaagtctta aagtgacctg acgtgaagg    4800 aaaaagtaag atgagaaata aagaaagcct ttgtaaggtg gttttaaaag ccttatatgc    4860
aaacctttta atctgtgttt ctgcaagtgc catccttgta cagtgttaag agggtaacat    4920
gggttacctt tgcaccagct tcagtgttaa gctcaccctg ttctttgaag cacccatgtc    4980
agtattagaa gaataggcag cagttcctta gtttacatat gtttgtgcaa ttattttctg    5040 tactttttg ttcattaatt ttgtcagtat tacaccaaac tgttttttgca acaaaaaaat    5100 tttttttgca ttcatttaat tttaggtcaa ataacatttt atttatgtgg ctcatttat    5160 atttcctaat tttatttatt tcatactgta gtgtacagta ttatagttct tcaatatata    5220
gatatatttt agtaaaaaag gaacatgacg ttgatcattt gggcaaattt tacgtaaaga    5280
gaagagcatt tattgtgttt tggaacatta attgtgagat gggatttttc aatttatta    5340 ttttatttt gttttttttcc aattactgga aattccaaat ttgggaactt ttgatacgat    5400
cttgtgaaaa cactgtattt tcgactgaaa attccacttt cttcatcttg ttttttagct    5460
aaaaagaggg actgttaaat acaatgtatg ataccatgac aaaaatcttt cctgaattgt    5520
ctttgtaaaa gtattattga atttcaatt tgtaatttct tttgaaaatg accatgctcg    5580
aataaaaatg tagccaaact aagaatgtag ttaatgagtt ctgtactttt agagagtttt    5640
ccttcaatga ccattaacat gtaacatgct ttatgcttat aataatgcta attatgtttt    5700
tttcatataa ttttagttta gcaataattt tgactggtac caataactgt ttttaaaat    5760 tccataccta tgtacagcaa ttttacagct tttctcaact gatcctgatt ccagattgtg    5820
tatttttatg tgaggttata ttattcaaat ttagtctatt tactttacag acatttctac    5880
ttttgcatta cgagtattta gagattatgt gttaaaaatt cacttctctg tccaaggggt    5940
ctttgtgatt tattcaaaaa aaagtctaat ttcaaaagaa cagctattat tcagtgttat    6000
ttataatatg taaccttttt taaaggattg ggatagttta tctcactttt tgaaatgcag    6060
acagtagttt accgtttatc tgaaactaga aggcgtgggt gggagaggaa aagctaaaag    6120
caaatgctaa caaaaataac cgtgattttc taagacagtt tttcagtttt tacaagatga    6180
ccctaatatt cagaatatga atgtattcgt aggttttaca taatgacttt tatcaagaaa    6240
ctagattctg cttcttaaat ctaattgcca agtgaagaat aacagaaaaa acagattacc    6300
ttatcaaatt tacagctctt gaatatacag aactataata tagtagctgt ccatgtattt    6360
```

```
tttctactttt agaatcaaag aagaaaagca tcattttgct attaaatttg ctaaaatttt    6420
gagtatgata tttccagttg gcaagaacaa catatttata tttattcctt agccataata    6480
ccactttcct aaatttcaca aaagtcattc tttgcaactt gaaactcaat agaaagtgtg    6540
tatgtgtgtg tgtgtatata tatatatata tacacacaca cacatacaca gaaaggatgt    6600
aatgaagata cagtaatagt tgagcagacc ttttagaaa aacatgtttt tagctctatc    6660 ttcaaactt ctggcagagg gggtggggg gcaggggga ggagtggcat caaaatgcta    6720
tgcctcctgt tatccacagc ctagagtttt tatatttgga aagtttagaa aattctatcc    6780
tcgtttctcc ttctttgaat ggcacaaata aatacactac ataaattttt ctggtttgaa    6840
aggctctagg cgataacttt attaattcaa cctgaaaata tcaagccatt aaattttgtc    6900
cgggtagaat aaatccctgt ggcctctttt aaagcaatgt aggtctctgt tgcccatggg    6960
gcatatctgt gtcccaatcc acaagagata ggaccaacaa acaatgaatg tgcaacctaa    7020
ctctttctcc ttggaaagaa gaaagtgtgc acgaagtaga ggagggtggg cagaccctgc    7080
cttgcccctc ctgttacccc cttctctgtc atttgttcct aactccattt cataggcagg    7140
ctcagaatac ctgagtctga aaatatcagg ataacacttg tgaattgtga caatcactac    7200
aatgtcccat atctgaggag ttttttttaa tgctatttat ccgctggaca cgattgcaca    7260
ttagggctgc ataatcctct aactctaggg aaaaataaaa acttttgatt tgtcttaaga    7320
ttcttctcca aggtcgcaaa caagaaattc ccctccacaa ccaagagatg tgcattttag    7380
taacatcaga tgtgttcttc tgttttatca actacttact cttcccacac gcttagttct    7440
aaatctaacc tttccccct cgaataggg gcagggagg atgaggaaac actggaacaa    7500
ctgaacaccc ctgcccattt tctccaagag ccttttgtat tctagcatat ctgtgcaatc    7560
ttttcttttt tcttcacatg acactgtaag cttaggcctg aaataactgg gaagagagat    7620
gcgtatcaga atttctccgc aagagctaaa caaaacatac atcttcctta gcatgaattg    7680 gactggggc ggagtgggag ggcttggagg aaagggggaaa gaagggacta tatttgaata    7740
aatatgaata aatgtattag atacttttca caatcagata acttttaaaa aggtcatttt    7800
ttatctttct aataatgtaa gccttaataa aagcaaatct tagtcacaaa tttgaggaga    7860
ctgcccaata ataagtttac atgtatttga actgaaaaat tgttaaccat gcttttgctc    7920
caagatgtgt gaggccattc agggggctgta gggccctgga tatacacaca acaagtgtg    7980 tgtatatctg gagccccaca cattgtaata aacacagctg catttatttg actatgtgat    8040
cccatgtaca tgtaaaaaca ttcaaacaaa cacactcagc ggatttattt attgtgcaat    8100
ggggcaatta ttcaaataaa catgctcaat gcaattattt gaatctcaca ttgcatgttc    8160
atcaatcata gcactaaaaa aagagggga aaaacacca aagaattcac atggggaaaa    8220
aatatatata tgaaaaccac cttattatag atttatagg gcagctgagg ttatggctcc    8280
cttcttaact gtaactcaac tattctgtat tcaatgacat ttgttttctaa tgattaattg    8340 gttcactcac ttgatcatat aatagcaaac tttataaacc tgtattgtgt agagatgtga    8400
aatctctata tttcaagagc agaagagttc tttctagaca ccttacatca agggacactg    8460
gtccaattat tatcgcttat ataagcactc ctataaattc tgaaaaattt tatacatgca    8520
acaaaacatt cctacatttg aagacattaa gaaaaatcac aggtgactca tctgatcatt    8580
ctatatatta ataaatatta tgacatatat gtgaacacat cacaaatcat attggtgtac    8640
caagaggcaa tttatgcctc tcttaagtat gtactgacat aacctaatat actaaaatgg    8700
gaaggggctt ttagtcactg aaatatgcat cgtgtaacaa agatgaagaa aatacatggc    8760
```

-continued

| | |
|---|---|
| ttgtgcccat cataaaaaaa gattcagact gaaggcttag ctttggtttt ttcaattaaa | 8820 |
| ttgttaaact gtgcacagtg atttttttt agaacttgag acatttgtga tgttggctgt | 8880 |
| ttaaatcttt gttaccttcg ctgtgaattg aaattgtaca tatttagtaa atcatgcaga | 8940 |
| caaaacaaac ttttagaca atatttttat tggagagttt tcttttcctg tatccatgtt | 9000 |
| aaaaaaaaaa aagacctcct ttcccaaaat aaaaatgtca atactaaatt taagaagta | 9060 |
| taaggaatg attgcttcct ttagagcaaa atatttaaat aaacatggag ataattggca | 9120 |
| acatgttctt tttgggctag taggctgtgt ccaattttt gggtctgatg tttcagaggg | 9180 |
| cctctgtttc agggttgaag atgatatatt aatctcggaa ttaaacaaat gctattaaat | 9240 |
| aac | 9243 |

<210> SEQ ID NO 4
<211> LENGTH: 1722
<212> TYPE: DNA
<213> ORGANISM: Homo sapiens

<400> SEQUENCE: 4

| | |
|---|---|
| attcattgcg ccgcggcacg gcctagcgag tggttcttct gcgctactgc tgcgcgaatc | 60 |
| ggcgacccca gtgcctcgac cactatgccg cgctcttttcc tcgtcaggaa gccctccgac | 120 |
| cccaatcgga agcctaacta cagcgagctg caggactcta atccagagtt taccttccag | 180 |
| cagccctacg accaggccca cctgctggca gccatcccac ctccggagat cctcaacccc | 240 |
| accgcctcgc tgccaatgct catctgggac tctgtcctgg cgcccaagc ccagccaatt | 300 |
| gcctgggcct cccttcggct ccaggagagt cccagggtgg cagagctgac ctccctgtca | 360 |
| gatgaggaca gtgggaaagg ctcccagccc ccagcccac cctcaccggc tccttcgtcc | 420 |
| ttctcctcta cttcagtctc ttccttggag gccgaggcct atgctgcctt cccaggcttg | 480 |
| ggccaagtgc ccaagcagct ggcccagctc tctgaggcca aggatctcca ggctcgaaag | 540 |
| gccttcaact gcaaatactg caacaaggaa tacctcagcc tgggtgccct caagatgcac | 600 |
| atccgaagcc acacgctgcc ctgcgtctgc ggaacctgcg ggaaggcctt ctctaggccc | 660 |
| tggctgctac aaggccatgt ccggacccac actggcgaga agcccttctc ctgtcccac | 720 |
| tgcagccgtg ccttcgctga ccgctccaac ctgcgggccc acctccagac ccactcagat | 780 |
| gtcaagaagt accagtgcca ggcgtgtgct cggaccttct cccgaatgtc cctgctccac | 840 |
| aagcaccaag agtccggctg ctcaggatgt ccccgctgac cctcgaggct ccctcttcct | 900 |
| ctccatacct gccccctgcct gacagccttc ccagctcca gcaggaagga ccccacatcc | 960 |
| ttctcactgc catggaattc cctcctgagt gccccacttc tggccacatc agccccacag | 1020 |
| gactttgatg aagaccattt tctggttctg tgtcctctgc ctgggctctg gaagaggcct | 1080 |
| tcccatggcc atttctgtgg agggagggca gctggcccc agccctgggg gattcctgag | 1140 |
| ctggcctgtc tgcgtgggtt tttgtatcca gagctgtttg gatacagctg ctttgagcta | 1200 |
| caggacaaag gctgacagac tcactgggaa gctcccaccc cactcagggg accccactcc | 1260 |
| cctcacacac acccccccac aaggaaccct caggccaccc tccacgaggt gtgactaact | 1320 |
| atgcaataat ccaccccag gtgcagcccc agggcctgcg gaggcggtgg cagactagag | 1380 |
| tctgagatgc cccgagccca ggcagctatt tcagcctcct gtttggtggg gtggcacctg | 1440 |
| tttcccggga aatttaacaa tgtctgaaaa gggactgtga gtaatggctg tcacttgtcg | 1500 |
| ggggcccaag tggggtgctc tggtctgacc gatgtgtctc ccagaactat tctgggggcc | 1560 |

```
cgacaggtgg gcctgggagg aagatgttta catttttaaa ggtacactgg tatttatatt    1620
tcaaacattt tgtatcaagg aaacgttttg tatagttata tgtacagttt attgatattc    1680
aataaagcag ttaattttata tattaaaaaa aaaaaaaaaa aa                      1722

<210> SEQ ID NO 5
<211> LENGTH: 4815
<212> TYPE: DNA
<213> ORGANISM: Homo sapiens

<400> SEQUENCE: 5
agtggcgtcg gaactgcaaa gcacctgtga gcttgcggaa gtcagttcag actccagccc      60
gctccagccc ggcccgaccc gaccgcaccc ggcgcctgcc ctcgctcggc gtccccggcc     120
agccatgggc ccttggagcc gcagcctctc ggcgctgctg ctgctgctgc aggtctcctc     180
ttggctctgc caggagccgg agccctgcca ccctggcttt gacgccgaga gctacacgtt     240
cacggtgccc cggcgccacc tggagagagg ccgcgtcctg ggcagagtga attttgaaga     300
ttgcaccggt cgacaaagga cagcctattt ttccctcgac acccgattca agtgggcac      360 agatggtgtg attacagtca aaaggcctct acggtttcat aacccacaga tccatttctt     420
ggtctacgcc tgggactcca cctacagaaa gttttccacc aaagtcacgc tgaatacagt     480
ggggcaccac caccgccccc cgccccatca ggcctccgtt tctggaatcc aagcagaatt     540
gctcacattt cccaactcct ctcctggcct cagaagacag aagagagact gggttattcc     600
tcccatcagc tgcccagaaa atgaaaaagg cccatttcct aaaaacctgg ttcagatcaa     660
atccaacaaa gacaaagaag gcaaggtttt ctacagcatc actggccaag agctgacac     720 accccctgtt ggtgtcttta ttattgaaag agaaacagga tggctgaagg tgacagagcc     780
tctggataga gaacgcattg ccacatacac tctcttctct cacgctgtgt catccaacgg     840
gaatgcagtt gaggatccaa tggagatttt gatcacggta accgatcaga tgacaacaa      900 gcccgaattc acccaggagg tctttaaggg gtctgtcatg gaaggtgctc ttccaggaac     960
ctctgtgatg gaggtcacag ccacagacgc ggacgatgat gtgaacacct acaatgccgc    1020
catcgcttac accatcctca gccaagatcc tgagctccct gacaaaaata tgttcacct     1080 taacaggaac acaggagtca tcagtgtggt caccactggg ctggaccgag agagtttccc    1140
tacgtatacc ctggtggttc aagctgctga ccttcaaggt gaggggttaa gcacaacagc    1200
aacagctgtg atcacagtca ctgacaccaa cgataatcct ccgatcttca atcccaccac    1260
gtacaagggt caggtgcctg agaacgaggc taacgtcgta atcaccacac tgaaagtgac    1320
tgatgctgat gcccccaata ccccagcgtg ggaggctgta tacaccatat tgaatgatga    1380
tggtggacaa tttgtcgtca ccacaaatcc agtgaacaac gatggcattt tgaaaacagc    1440
aaagggcttg gattttgagg ccaagcagca gtacattcta cacgtagcag tgacgaatgt    1500 ggtaccttt gaggtctctc tcaccactct cacagccacc gtcaccgtgg atgtgctgga    1560
tgtgaatgaa gcccccatct tgtgcctcc tgaaaagaga gtggaagtgt ccgaggactt    1620
tggcgtgggc caggaaatca catcctacac tgcccaggag ccagacacat ttatggaaca    1680
gaaaataaca tatcggattt ggagagacac tgccaactgg ctggagatta tccggacac     1740 tggtgccatt tccactcggg ctgagctgga cagggaggat tttgagcacg tgaagaacag    1800
cacgtacaca gccctaatca tagctacaga caatggttct ccagttgcta ctggaacagg    1860
gacacttctg ctgatcctgt ctgatgtgaa tgacaacgcc cccatccag aacctcgaac     1920 tatattcttc tgtgagagga atccaaagcc tcaggtcata aacatcattg atgcagacct    1980
```

```
tcctcccaat acatctccct tcacagcaga actaacacac ggggcgagtg ccaactggac    2040
cattcagtac aacgacccaa cccaagaatc tatcattttg aagccaaaga tggccttaga    2100
ggtgggtgac tacaaaatca atctcaagct catggataac cagaataaag accaagtgac    2160
caccttagag gtcagcgtgt gtgactgtga aggggccgct ggcgtctgta ggaaggcaca    2220
gcctgtcgaa gcaggattgc aaattcctgc cattctgggg attcttggag gaattcttgc    2280
tttgctaatt ctgattctgc tgctcttgct gtttcttcgg aggagagcgg tggtcaaaga    2340
gcccttactg cccccagagg atgacacccg ggacaacgtt tattactatg atgaagaagg    2400
aggcggagaa gaggaccagg actttgactt gagccagctg cacagggggcc tggacgctcg    2460 gcctgaagtg actcgtaacg acgttgcacc aaccctcatg agtgtccccc ggtatcttcc    2520 ccgcccctgcc aatcccgatg aaattggaaa ttttattgat gaaaatctga agcggctga    2580 tactgacccc acagcccgc cttatgattc tctgctcgtg tttgactatg aaggaagcgg    2640
ttccgaagct gctagtctga gctccctgaa ctcctcagag tcagacaaag accaggacta    2700
tgactacttg aacgaatggg gcaatcgctt caagaagctg gctgacatgt acggaggcgg    2760
cgaggacgac taggggactc gagagaggcg ggccccagac ccatgtgctg ggaaatgcag    2820
aaatcacgtt gctggtggtt tttcagctcc cttcccttga tgagtttc tggggaaaaa    2880 aaagagactg gttagtgatg cagttagtat agctttatac tctctccact ttatagctct    2940 aataagttg tgttagaaaa gtttcgactt atttcttaaa gcttttttt ttttcccatc    3000 actctttaca tggtggtgat gtccaaaaga tacccaaatt ttaatattcc agaagaacaa    3060
ctttagcatc agaaggttca cccagcacct tgcagatttt cttaaggaat tttgtctcac    3120
ttttaaaaag aaggggagaa gtcagctact ctagttctgt tgttttgtgt atataatttt    3180
ttaaaaaaaa tttgtgtgct tctgctcatt actacactgg tgtgtccctc tgccttttt    3240 ttttttttaa gacagggtct cattctatcg gccaggctgg agtgcagtgg tgcaatcaca    3300
gctcactgca gccttgtcct cccaggctca agctatcctt gcacctcagc ctcccaagta    3360
gctgggacca caggcatgca ccactacgca tgactaattt tttaaatatt tgagacgggg    3420
tctccctgtg ttacccaggc tggtctcaaa ctcctgggct caagtgatcc tcccatcttg    3480
gcctcccaga gtattgggat tacagacatg agccactgca cctgcccagc tccccaactc    3540
cctgccattt tttaagagac agtttcgctc catcgcccag gctgggatg cagtgatgtg    3600 atcatagctc actgtaacct caaactctgg ggctcaagca gttctcccac cagcctcctt    3660 tttattttt tgtacagatg gggtcttgct atgttgccca agctggtctt aaactcctgg    3720
cctcaagcaa tccttctgcc ttggcccccc aaagtgctgg gattgtgggc atgagctgct    3780
gtgcccagcc tccatgtttt aatatcaact ctcactcctg aattcagttg ctttgcccaa    3840
gataggagtt ctctgatgca gaaattattg ggctctttta gggtaagaag tttgtgtctt    3900
tgtctggcca catcttgact aggtattgtc tactctgaag acctttaatg gcttccctct    3960
ttcatctcct gagtatgtaa cttgcaatgg gcagctatcc agtgacttgt tctgagtaag    4020
tgtgttcatt aatgtttatt tagctctgaa gcaagagtga tatactccag gacttagaat    4080
agtgcctaaa gtgctgcagc caaagacaga gcggaactat gaaaagtggg cttggagatg    4140
gcaggagagc ttgtcattga gcctggcaat ttagcaaact gatgctgagg atgattgagg    4200
tgggtctacc tcatctctga aaattctgga aggaatggag gagtctcaac atgtgttttct    4260 gacacaagat ccgtggtttg tactcaaagc ccagaatccc caagtgcctg cttttgatga    4320
```

| | |
|---|---|
| tgtctacaga aaatgctggc tgagctgaac acatttgccc aattccaggt gtgcacagaa | 4380 |
| aaccgagaat attcaaaatt ccaaattttt ttcttaggag caagaagaaa atgtggccct | 4440 |
| aaaggggtt agttgagggg taggggtag tgaggatctt gatttggatc tcttttatt | 4500 |
| taaatgtgaa tttcaacttt tgacaatcaa agaaaagact tttgttgaaa tagctttact | 4560 |
| gtttctcaag tgttttggag aaaaaaatca accctgcaat cacttttgg aattgtcttg | 4620 |
| attttcggc agttcaagct atatcgaata tagttctgtg tagagaatgt cactgtagtt | 4680 |
| ttgagtgtat acatgtgtgg gtgctgataa ttgtgtattt tctttggggg tggaaaagga | 4740 |
| aaacaattca agctgagaaa agtattctca aagatgcatt tttataaatt ttattaaaca | 4800 |
| attttgttaa accat | 4815 |

<210> SEQ ID NO 6
<211> LENGTH: 6278
<212> TYPE: DNA
<213> ORGANISM: Homo sapiens

<400> SEQUENCE: 6

| | |
|---|---|
| tttctccctc ccctctggga tgcgaaacgc gaggttttgt aacctttcct ggcaattta | 60 |
| gattttgtgt gggatttcct gtctagaagc agatacgaag attttaagc tgtttcaaga | 120 |
| tgtttccttc caatccataa ttatatttt aatatattcg agccatcatt aaaatcactg | 180 |
| ctttcgtgat tttaattatt caaataaaca cttgcatttt aaagacgtct gttgattata | 240 |
| aacgaaaggt attttggtat tctcattgtg gagagatgac ttgttatagc aaggagtgga | 300 |
| gcataggcta ttgcaatttt aatttcctgt tttagcgtca aatagtgtgt gttccatatt | 360 |
| gagctgttgc cgctgttgct gatgtggctt tatgaaagtt acaaattata atactgtggt | 420 |
| agaaacaaat tcagattcag atgatgaaga caaactgcat attgtggaag aagaaagtgt | 480 |
| tacagatgca gctgactgtg aaggtgtacc agaggatgac ctgccaacag accagacagt | 540 |
| gttaccaggg aggagcagtg aaagagaagg gaatgctaag aactgctggg aggatgacac | 600 |
| aggaaaggaa gggcaagaaa tcctggggcc tgaagctcag gcagatgaag caggatgtac | 660 |
| agtaaaagat gatgaatgcg agtcagatgc agaaaatgag caaaaccatg atcctaatgt | 720 |
| tgaagagttt ctacaacaac aagacactgc tgtcattttt cctgaggcac ctgaagagga | 780 |
| ccagaggcag ggcacaccag aagccagtgg tcatgatgaa aatggaacac cagatgcatt | 840 |
| ttcacaatta ctcacctgtc catattgtga tagaggctat aaacgcttta cctctctgaa | 900 |
| agaacacatt aaatatcgtc atgaaaagaa tgaagataac tttagttgct ccctgtgcag | 960 |
| ttacaccttt gcatacagaa cccaacttga acgtcacatg atcatacata aatcaggaag | 1020 |
| agatcaaaga catgtgacgc agtctgggtg taatcgtaaa ttcaaatgca ctgagtgtgg | 1080 |
| aaaagctttc aaatacaaac atcacctaaa agagcactta agaattcaca gtggagagaa | 1140 |
| gccatatgaa tgcccaaact gcaagaaacg cttttcccat tctggctcct atagctcaca | 1200 |
| cataagcagt aagaaatgta tcagcttgat acctgtgaat gggcgaccaa gaacaggact | 1260 |
| caagacatct cagtgttctt caccgtctct ttcagcatca ccaggcagtc ccacacgacc | 1320 |
| acagatacgg caaagatag agaataaacc ccttcaagaa caactttctg ttaaccaaat | 1380 |
| taaaactgaa cctgtggatt atgaattcaa acccatagtg gttgcttcag gaatcaactg | 1440 |
| ttcaaccct ttacaaaatg gggttttcac tggtggtggc ccattacagg caaccagttc | 1500 |
| tcctcagggc atggtgcaag ctgttgttct gccaacagtt ggtttggtgt ctcccataag | 1560 |
| tatcaattta agtgatattc agaatgtact taaagtggcg gtagatggta atgtaataag | 1620 |

```
gcaagtgttg gagaataatc aagccaatct tgcatccaaa gaacaagaaa caatcaatgc   1680
ttcacccata caacaaggtg gccattctgt tatttcagcc atcagtcttc ctttggttga   1740
tcaagatgga acaaccaaaa ttatcatcaa ctacagtctt gagcagccta gccaacttca   1800
agttgttcct caaaatttaa aaaagaaaa tccagtcgct acaaacagtt gtaaaagtga    1860
aaagttacca gaagatctta ctgttaagtc tgagaaggac aaaagctttg aaggggggt    1920 gaatgatagc acttgtcttc tgtgtgatga ttgtccagga gatattaatg cacttccaga   1980
attaaagcac tatgacctaa agcagcctac tcagcctcct ccactccctg cagcagaagc   2040
tgagaagcct gagtcctctg tttcatcagc tactggagat ggcaatttgt ctcctagtca   2100 gccacccttta aagaacctct tgtctctcct aaaagcatat tatgctttga atgcacaacc   2160
aagtgcagaa gagctctcaa aaattgctga ttcagtaaac ctaccactgg atgtagtaaa   2220
aaagtggttt gaaaagatgc aagctggaca gatttcagtg cagtcttctg aaccatcttc   2280
tcctgaacca ggcaaagtaa atatccctgc caagaacaat gatcagcctc aatctgcaaa   2340
tgcaaatgaa ccccaggaca gcacagtaaa tctacaaagt cctttgaaga tgactaactc   2400 cccagttttta ccagtgggat caaccaccaa tggttccaga agtagtacac catccccatc   2460
acctctaaac ctttcctcat ccagaaatac acagggttac ttgtacacag ctgagggtgc   2520
acaagaagag ccacaagtag aacctcttga tctttcacta ccaaagcaac agggagaatt   2580
attagaaagg tcaactatca ctagtgttta ccagaacagt gtttattctg tccaggaaga   2640
acccttgaac ttgtcttgcg caaaaaagga gccacaaaag gacagttgtg ttacagactc   2700
agaaccagtt gtaaatgtaa tcccaccaag tgccaacccc ataaatatcg ctatacctac   2760
agtcactgcc cagttaccca aatcgtggc cattgctgac cagaacagtg ttccatgctt    2820
aagagcgcta gctgccaata agcaaacgat tctgattccc caggtggcat acacctactc   2880
aactacggtc agccctgcag tccaagaacc cccttgaaaa gtgatccagc caaatggaaa   2940
tcaggatgaa agacaagata ctagctcaga aggagtatca aatgtagagg atcagaatga   3000
ctctgattct acaccgccca aaaagaaaat gcggaagaca gaaaatggaa tgtatgcttg   3060
tgatttgtgt gacaagatat tccaaaagag tagttcatta ttgagacata aatatgaaca   3120
cacaggtaaa agacctcatg agtgtggaat ctgtaaaaag gcatttaaac acaaacatca   3180
tttgattgaa cacatgcgat tacattctgg agaaaagccc tatcaatgtg acaaatgtgg   3240
aaagcgcttc tcacactctg gtctttattc tcaacacatg aatcatcgct actcctactg   3300
taagagagaa gcgaagaac gtgacagcac agagcaggaa gaggcagggc ctgaaatcct    3360
ctcgaatgag cacgtgggtg ccagggcgtc tccctcacag ggcgactcgg acgagagaga   3420
gagtttgaca agggaagagg atgaagacag tgaaaaagag gaagaggagg aggataaaga   3480
gatggaagaa ttgcaggaag aaaaagaatg tgaaaaacca caagggatg aggaagagga    3540 ggaggaggag gaagaagtgg aagaagaaga ggtagaagag gcagagaatg agggagaaga   3600
agcaaaaact gaaggtctga tgaaggatga cagggctgaa agtcaagcaa gcagcttagg   3660
acaaaaagta ggcgagagta gtgagcaagt gtctgaagaa aagacaaatg aagcctaatc   3720 gttttctag aaggaaaata aattctaatt gataatgaat ttcgttcaat attatccttg    3780
cttttcatgg aaacacagta acctgtatgc tgtgattcct gttcactact gtgtaaagta   3840
aaaactaaaa aatacaaaa tacaaaacac acacacacac acacacacac acacacacac   3900
acacacaaaa taaatccggg tgtgcctgaa cctcagacct agtaattttt catgcagttt   3960
```

```
tcaaagttag gaacaagttt gtaacatgca gcagattaga aaaccttaat gactcagaga    4020
gcaacaatac aagaggttaa aggaagctga ttaattagat atgcatctgg cattgtttta    4080
tcttatcagt attatcactc ttatgttggt ttattcttaa gctgtacaat tgggagaaat    4140
tttataattt tttattggta aacatatgct aaatccgctt cagtatttta ttatgttttt    4200
taaaatgtga gaacttctgc actacaaaat tcccttcaca gagaagtata atgtagttcc    4260
aacccgtgct aactaccttt tataaattca gtctagaagg tagtaatttc taatatttag    4320
atgtcttagt agagcgtatt atcatttaaa gtgtattgtt agccttaaga aagcagctga    4380
tagaagaact gaagtttctt actcacgtgg tttaaaatgg agttcaaaag attgccattg    4440
agttctgatt gcagggacta acaatgttaa tctgataagg acagcaaaat catcagaatc    4500
agtgtttgtg attgtgtttg aatatgtggt aacatatgaa ggatatgaca tgaagctttg    4560
tatctccttt ggccttaagc aagacctgtg tgctgtaagt gccatttctc agtattttca    4620
aggctctaac ccgccttcat ccaatgtgtg cctacaata actagcattt gttgatttgt    4680
ctcttgtatc aaaattccca aataaaactt aaaaccactg actctgtcag agaaactgaa    4740
acactgggac atttcatcct tcaattcctc ggtattgatt ttatgttgat tgattttcag    4800
aatttctcta cagaaacgaa agggaaattt tctaatctgc tttatccatg tacttgcatt    4860
tcagacatgg acatgctatt gttatttggc tcataactgt ttccaaatgt tagttattat    4920
ggacccaatt tattaacaac attagctgat ttttacctat cagtattatt ttatttcttt    4980
tagtttatag atctgtgcaa cattttttgta ctgtatgtct tcaaacctgg cagtattaat    5040
acccttctta ctgacatatg tacttttagt tttagaaaac ttttatattt atgtgtctta    5100
tttttatatt tctttatttta ttacacagtg tagtgtataa tactgtagtt tgtattaata    5160
caataatata tttagtatg aaaatttgga aagttgataa gatttaaagt agagatgcaa    5220
ttggttctcc tgcattgaga tttgatttaa cagtgttatg ttaacattta tacttgcctt    5280
ggactgtaga acagaactta aatgggaatg tattagtttt acaactacaa tcaagtcatt    5340
ttacctttac ccagttttta atataaaact taaattttga aattcactgt gtgactaata    5400
gcatgatgct ctgcagtttt attaagaaat cagcctaacc atacaactct catttcctta    5460
gtaagccaaa ttaggattaa cttctataaa cagtgttggg aacaatgttt aacattttgt    5520
gccaatttgt tcctgtattc atgtatgtaa gttacagatc tgactcttca ttttaagtt    5580 ccttgttaca tcatggtcat tttctagttt tttaccagac tcccatctca caataaaatg    5640
catcaacaag cctgaactgc tgtcattctt ttcatcatta tcagtatttt ctttggaaaa    5700
ctgtgaaatg gggtacattg tcatcctgca tttgattcat cttgagctga atttgggtaa    5760
cactaaatgt tttagacatt ctccactaaa ttatggattt tcttgtggct aaatgtttct    5820
ggagaggtca gagttgacaa aacctcttca caggttgctc cttcttcctg aaatccttaa    5880
tcctccgcat ttcatgcttc aggtcatttc agggaagcct gggtttagat gcctttctga    5940
ctctcagctc ctgcacttct gtcatcatac ctctgatact attatttata ttccttcccc    6000
actaggaaca ggaaccacat ttgtcatagt cactctcaca ttcctcactg cctaacaggg    6060
tgcctggcat aagttgggac aacagatatt tgttgaataa aaatataatt tgcatgttta    6120
tggagctcag ctatgttctc acttttttg cttctaattc cagaatatat gttaaatgat    6180
ctaataattt gattatttc ttataagtct tattaaacac tagtcataat agacacaata    6240
aattatgcct tcttttcta ttgccttaaa aaaaaaa                              6278
```

<210> SEQ ID NO 7
<211> LENGTH: 4071
<212> TYPE: DNA
<213> ORGANISM: Homo sapiens

<400> SEQUENCE: 7

| | | | | | |
|---|---|---|---|---|---|
| tgattcgagc | gggaagaggg | gggtgggtgg | gatcggtggg | ggagaccatg | acctccagct | 60 |
| acgggcacgt | tctggagcgg | caaccggcgc | tgggcggccg | cttggacagc | ccgggcaacc | 120 |
| tcgacaccct | gcaggcgaaa | aagaacttct | ccgtcagtca | cctgctagac | ctggaggaag | 180 |
| ccggggacat | ggtggcggca | caggcggatg | agaacgtggg | cgaggctggc | cggagcctgc | 240 |
| tggagtcgcc | gggactcacc | agcggcagcg | acaccccgca | gcaggacaat | gaccagctga | 300 |
| actcagaaga | aaaaagaag | agaaagcagc | gaaggaatag | gacaaccttc | aatagcagcc | 360 |
| agctgcaggc | tttggagcgt | gtctttgagc | ggacacacta | tcctgatgct | tttgtgcgag | 420 |
| aagaccttgc | ccgccgggtg | aacctcaccg | aggcgagagt | gcaggtgtgg | tttcagaacc | 480 |
| gaagagccaa | gttccgcagg | aatgagagag | ccatgctagc | caataaaaac | gcttccctcc | 540 |
| tcaaatccta | ctcaggagac | gtgactgctg | tggagcagcc | catcgtacct | cgtcctgctc | 600 |
| cgagacccac | cgattatctc | tcctggggga | cagcgtctcc | gtacagatcc | tcgtccctcc | 660 |
| caagatgttg | tttacacgag | gggcttcata | acggattcta | acggaagaca | ctgaaaagcg | 720 |
| ccatggctac | ttattctgcc | acatgtgcca | acaatagccc | tgcacagggc | atcaacatgg | 780 |
| ccaacagcat | tgccaacctg | agactgaagg | ccaaggaata | tagtttacag | aggaaccagg | 840 |
| tgccaacagt | caactgagga | aaaaaataa | ttaaacaggc | taagaagaa | atcaaaaacc | 900 |
| ataagacacc | tatcctgctc | tgttatttct | tcatctgctg | gggggaaaaa | gtaaattaca | 960 |
| aacaaacaaa | caaagcagaa | ctaaaatatt | gggaccatgg | cagagaaaag | caggagagga | 1020 |
| gcaaaatgaa | aattagttaa | caaatgttcc | tcctccctct | gggataccac | caccacttgt | 1080 |
| ttctgtgtgt | gtttattttg | tttttctttc | attcatgctt | tgcttaatgt | actccaggct | 1140 |
| tcttcagcta | ggttcagccc | acccaccccc | atgattgtat | gaagttttaa | aaaaaactac | 1200 |
| agcagccaaa | gaaactatat | atatatatat | atatatatat | atccagaatg | attgcctcta | 1260 |
| ctgtcctcat | tgacttgttt | gaaccttagt | gccttaccct | gtcctcttcc | cagttctctt | 1320 |
| tatagaagct | ctaggagctt | tcgaaaagcc | aaagtctttc | tgaagaatct | gtgctggaca | 1380 |
| gacataattc | cctttctcat | tgtctccatc | tttgttggtc | atggtaaggt | ttttccatca | 1440 |
| gcctctgaaa | aaatagttgt | gcacaacatc | tgctcactgg | actgtctgat | ccaatgtaat | 1500 |
| tggctgcgtc | tggctaattc | taagcactaa | agtctacatc | taagctatag | atttaagctt | 1560 |
| gaagctacag | attatatcac | tatcaccacc | acccctcacc | ctatgcaatc | aatcaatcaa | 1620 |
| tcatcttaag | ttaaagatat | ttgttgtctt | tgaatgattt | gctgtcacag | actatttggt | 1680 |
| agaagaaata | ttttcacct | gagagaggaa | gagaaatttc | tctagtaaca | caaagagtga | 1740 |
| gttctaaaag | gcatgccac | atctctttcg | tgccttaagg | atagtgagat | gcacacttat | 1800 |
| atatatactg | tatatattta | tatatttata | tatatatttc | atatatatat | ataatattgc | 1860 |
| aagcttaagt | ttgcaatttc | ccaaacaata | caaaaagcaa | attacacacc | ctcaccactg | 1920 |
| ttcttatctc | tatagtgatg | aaacattaat | tagggatctt | gctgcttttc | ttttctaca | 1980 |
| cgaagttttc | attaaagcca | cagaataatt | gatagggcag | ctgtttgaga | acaggtccca | 2040 |
| ttttcacatt | agggctttaa | atgaattaga | aactatttga | ggctataaaa | atgtccttga | 2100 |
| gtttggagcc | tgagctctgg | tgaaatgctg | atacatctga | tctatcatgg | gaattgcagt | 2160 |

-continued

| | |
|---|---|
| tagagagagt aaggaatacc atttagtcat ctatccgttc ttcacttagc aggaatatga | 2220 |
| aagaaaggca catgtttaag aggaatacct aaaggttttt ctaaattcca acatttaaaa | 2280 |
| ggcaattgtg ggctattttt atttttaat attttgaaat aaagtttagt gtctagggct | 2340 |
| gggagccagg actgatcttc catttctttt tctttgttcc cagccatgct tttgtaactt | 2400 |
| gccaggtgga cttgaccaac tacattacca tgctgtgcct cagtttaccc atttgtaaaa | 2460 |
| tgggattaat aatacttacc tacctcacag gggtgttgtg aggctctatt catttgctcc | 2520 |
| tttattcttt cctgtattct ctgtatgtcc agcactttgt agccatggga ggaaagggac | 2580 |
| tataaaagtg tacaatgtta atggaatgat acggtacctg aaagccttgt tttctagtaa | 2640 |
| gaaaatgcta ccttgctgta catacttata accttgtatt tggaaatgag aaataggttt | 2700 |
| atattttcag atctctcaaa aatcacatca tttgaccaaa gaataattta agacacatag | 2760 |
| aacagatttt tttaatttat attttcatcc tgaccagctt agttctaata attttttagtt | 2820 |
| gtgagtgatt aaaaaacttt ggatcaattt tggtcaaaca tgccaacttt gtagtctgag | 2880 |
| tgacaggcaa ggattttgg gtttaagatg cactttagc acacatttgt atttcccttg | 2940 |
| gcatatcaga ttgagctaat ggtgatgtta tttcaatcta acagccacca atctgaaatt | 3000 |
| gtatttcaaa tgttgattct gtagttcttt aaataataat gaagctcatc ttatacattt | 3060 |
| tgcttttcacc aattgattcc ttcttctttt agcccactat taaaacatttt cttactgaat | 3120 |
| ggttcatgta ggcttgctga acagcacgca ttacttgctt cctgaagagt tcccccattc | 3180 |
| atccatttgt cccattagtt gctgtggatt atcaagtttt gaaggaactg tacatcccaa | 3240 |
| cagactgaaa cattctaagt gaaatgagta taatccaagt aactggtgaa ctttggaggt | 3300 |
| ttggagcttg aagagaatgg ctaagaagat ttgaattata gggagggaac agaaatcata | 3360 |
| catgaaaagg ttttactgag aagggggaaa ccttagatag agggacatgt gaaacaaaat | 3420 |
| catttgaaat tttgattcag acatccatttt ccagtggcaa acagcaaagc ctgaacccat | 3480 |
| aaacccaaat gataggtgaa gttgggtggt tttatccaat gtctcaagca agcaatgtct | 3540 |
| gggaatatca tagagtaaca agtgctggtc agccaaagaa acattcactg ctggtgaacc | 3600 |
| aataccataa gcatgtatta tctaagcact tgatcaagaa atatacatgt tgtacaagct | 3660 |
| ctcaattttg ttcatttatt atcaaatttt taaaatacaa gtttggtatg tgatttggaa | 3720 |
| aagatgcctt ctggatctta agccagttgt cagtggaggt cctcagggct gcaaatgtca | 3780 |
| agacataacc ctgttcctca ccatcatgat accagataca ggtgaataca taggaactat | 3840 |
| ctgcctgtgt cctcaatctc ccttcaaaca agatgctgat ttgtagggta cttggcaggt | 3900 |
| taaattaaac cagaagaggt gacttaataa aaaagggaat gacatttagg gtataaagat | 3960 |
| ctcataagaa atgtaatatg taaattatat cttgctttat gttgtaaaat atacattgtt | 4020 |
| tgcgctagaa tagaaatgat ttcttttcaa taaaagaaa gaaggactct a | 4071 |

<210> SEQ ID NO 8
<211> LENGTH: 3626
<212> TYPE: DNA
<213> ORGANISM: Homo sapiens

<400> SEQUENCE: 8

| | |
|---|---|
| ttattaatcc cacaagattg tgtgaatgtg tactccgagc caggcacgtt ggacttctaa | 60 |
| cttcctctta gcccaagtag gaaggggaga ctcaggcgct ggggaccatt ctcctctccc | 120 |
| tgcagcagag ttgcagtccc tatccctcct gggtgcccat ccccgtgcct attttcctgg | 180 |
| atccccaccc agttgatgtg acaggctcgt ggcccaatcc ccttcctggt tcccaggccg | 240 |

```
actgctagca ccacccgagc caatggcggc ggccgagggg cggaggggc tggcaggagg      300
ggagggagcg ctggctttag agccacagct gcaaagattc cgaggtgcag aagttgtctg      360
agtgggttgg tcggcggcag tcgggccaga cccaggactc tgcgacttta catctttaaa      420
tggatgagat ggctaccact cagatttcca aagatgagct tgatgaactc aaagaggcct      480
ttgcaaaagt tgatctcaac agcaacggat tcatttgtga ctatgaactt catgagctct      540
tcaaggaagc taatatgcca ttaccaggat ataaagtgag agaaattatt cagaaactca      600
tgctggatgg tgacaggaat aaagatggga aaataagttt tgacgaattt gtttatattt      660
ttcaagaggt aaaagtagt gatattgcca agaccttccg caaagcaatc aacaggaaag      720
aaggtatttg tgctctgggt ggaacttcag agttgtccag cgaaggaaca cagcattctt      780
actcagagga agaaaaatat gcttttgtta actggataaa caaagctttg gaaaatgatc      840
ctgattgtag acatgttata ccaatgaacc ctaacaccga tgacctgttc aaagctgttg      900
gtgatggaat tgtgctttgt aaaatgatta acctttcagt tcctgatacc attgatgaaa      960
gagcaatcaa caagaagaaa cttacaccct tcatcattca ggaaaacttg aacttggcac     1020
tgaactctgc ttctgccatt gggtgtcatg ttgtgaacat tggtgcagaa gatttgaggg     1080
ctgggaaacc tcatctggtt ttgggactgc tttggcagat cattaagatc ggtttgttcg     1140
ctgacattga attaagcagg aatgaagcct tggctgcttt actccgagat ggtgagactt     1200
tggaggaact tatgaaattg tctccagaag agcttctgct tagatgggca aactttcatt     1260
tggaaaactc gggctggcaa aaaattaaca actttagtgc tgacatcaag gattccaaag     1320
cctatttcca tcttctcaat caaatcgcac caaaaggaca aaaggaaggt gaaccacgga     1380
tagatattaa catgtcaggt ttcaatgaaa cagatgattt gaagagagct gagagtatgc     1440
ttcaacaagc agataaatta ggttgcagac agtttgttac ccctgctgat gttgtcagtg     1500
gaaaccccaa actcaactta gctttcgtgg ctaacctgtt taataaatac ccagcactaa     1560
ctaagccaga gaaccaggat attgactgga ctctattaga aggagaaact cgtgaagaaa     1620
gaaccttccg taactggatg aactctcttg gtgtcaatcc tcacgtaaac catctctatg     1680
ctgacctgca agatgccctg gtaatcttac agttatatga acgaattaaa gttcctgttg     1740
actggagtaa ggttaataaa cctccatacc cgaaactggg agccaacatg aaaaagctag     1800
aaaactgcaa ctatgctgtt gaattaggga agcatcctgc taaattctcc ctggttggca     1860
ttggagggca agacctgaat gatgggaacc aaaccctgac tttagcttta gtctggcagc     1920
tgatgagaag atataccctc aatgtcctgg aagatcttgg agatggtcag aaagccaatg     1980
acgacatcat tgtgaactgg gtgaacagaa cgttgagtga agctggaaaa tcaacttcca     2040
ttcagagttt taaggacaag acgatcagct ccagtttggc agttgtggat ttaattgatg     2100
ccatccagcc aggctgtata aactatgacc ttgtgaagag tggcaatcta acagaagatg     2160
acaagcacaa taatgccaag tatgcagtgt caatggctag aagaatcgga gccagagtgt     2220
atgctctccc tgaagacctt gtggaagtaa agcccaagat ggtcatgact gtgtttgcat     2280
gtttgatggg caggggaatg aagagagtgt aaaataacca atctgaataa aacagccatg     2340
ctcccaggtg catgattcgc aggtcagcta tttccaggtg aagtgcttat ggcttaagga     2400
actcttggcc attcaaagga ctttttcattt tgattaacag gactagctta tcatgagagc     2460
cctcagggga aagggtttaa gaaaacaac tcctctttcc catagtcaga gttgaatttg     2520
tcaggcacgc ctgaaatgtg ctcatagcca aaacatttta ctctctcctc ctagaatgct     2580
```

```
gcccttgaca tttcccattg ctgtatgtta tttcttgctc tgttatcttt tgccctctta    2640
gaatgtccct ctcttgggac ttgcttagat gatgggatat gaatattatt agacagtaat    2700
tttgctttcc atccagtatg ctagttctta ttcgagaact atggtcagag cgtatttgga    2760
tatgagtatc ctttgcttat cttttgtagta ctgaaaattt gccgaagtaa ctggctgtgc    2820
agaatgtaat agaagctttt cttattcttt tattcttaag atcagtatct ttttacagta    2880
ttctttctac atgatccttt tttgtacatt taagaatatt ttgattatat aaacaagac    2940 tgctgatttt gctactttt ttaaggggtc ttcaagtaag taaaacatac atcgtagcta    3000
gaagaaaaat gtaccttaaa tttgcatctt ccctctcata cccaagctgt aaacaattga    3060
aatattttgt cttaaatcac ttggttcaat acatgcttat ttgttttaaa acctgtatca    3120
tcaaactctc tctctaaatt taaaatgctg ttgaatatga acttttgag gagagagtgt    3180 gctcagaact tagacgggat ttggtaggcc aagtatgcta agtgtacaat atatttttta    3240
attttacacc tgaaacaaag aaatgtggtc actaaaaata aaagtatata tgtaggaatt    3300
aatgtactct tgctttgtca agctgtttgc tatagtttcc aaggtattat gttactctaa    3360
ctctgaaaag tgatgtaatc tggtagcaat gtagtagttc aaataaaggc atttacataa    3420
taattagtct gttcttcatg cttttgtctc ttaggaagta tgccaatgtt tgtcaggatt    3480
tttttctttt tgttttctg atgtattctg taaaatggtg tttgttaaat ttgagttttg    3540
ggagctgaat tagaggtact gaattaagga cagtacaaat gaagtaaaaa ggttttctcc    3600
aatttaccaa aaaaaaaaaa aaaaaa                                        3626

<210> SEQ ID NO 9
<211> LENGTH: 21
<212> TYPE: DNA
<213> ORGANISM: Artificial Sequence
<220> FEATURE:
<223> OTHER INFORMATION: synthetic primer

<400> SEQUENCE: 9
cgccgctaga ggtgaaattc t                                                 21

<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10
ctttcgctct ggtccgtctt                                                   20

<210> SEQ ID NO 11
<211> LENGTH: 1969
<212> TYPE: DNA
<213> ORGANISM: Homo sapiens
<220> FEATURE:
<221> NAME/KEY: misc_feature
<222> LOCATION: (57)..(61)
<223> OTHER INFORMATION: n is a, c, g, or t

<400> SEQUENCE: 11
ccgtccgtcc gtcgtcctcc tcgcttgcgg ggcgccgggc ccgtcctcga gccccnnnn     60 nccgtccggc cgcgtcgggg cctcgccgcg ctctacctac ctacctggtt gatcctgcca    120
gtagcatatg cttgtctcaa agattaagcc atgcatgtct aagtacgcac ggccggtaca    180
gtgaaactgc gaatggctca ttaaatcagt tatggttcct ttggtcgctc gctcctctcc    240
```

```
tacttggata actgtggtaa ttctagagct aatacatgcc gacgggcgct gaccccttc      300 gcggggggga tgcgtgcatt tatcagatca aaaccaaccc ggtcagcccc tctccggccc      360
cggccggggg gcgggccgcg gcggctttgg tgactctaga taacctcggg ccgatcgcac      420
gccccccgtg gcggcgacga cccattcgaa cgtctgccct atcaactttc gatggtagtc      480
gccgtgccta ccatggtgac cacgggtgac ggggaatcag ggttcgattc cggagaggga      540
gcctgagaaa cggctaccac atccaaggaa ggcagcaggc gcgcaaatta cccactcccg      600
acccggggag gtagtgacga aaaataacaa tacaggactc tttcgaggcc ctgtaattgg      660
aatgagtcca ctttaaatcc tttaacgagg atccattgga gggcaagtct ggtgccagca      720
gccgcggtaa ttccagctcc aatagcgtat attaaagttg ctgcagttaa aaagctcgta      780
gttggatctt gggagcgggc gggcggtccg ccgcgaggcg agccaccgcc cgtcccccgcc     840 ccttgcctct cggcgccccc tcgatgctct tagctgagtg tcccgcgggg cccgaagcgt      900
ttactttgaa aaaattagag tgttcaaagc aggcccgagc cgcctggata ccgcagctag      960
gaataatgga ataggaccgc ggttctatt tgttggtttt cggaactgag gccatgatta     1020
agagggacgg ccgggggcat tcgtattgcg ccgctagagg tgaaattctt ggaccggcgc     1080
aagacggacc agagcgaaag catttgccaa gaatgttttc attaatcaag aacgaaagtc     1140
ggaggttcga agacgatcag ataccgtcgt agttccgacc ataaacgatg ccgaccggcg     1200
atgcggcggc gttattccca tgacccgccg ggcagcttcc gggaaaccaa agtctttggg     1260
ttccgggggg agtatggttg caaagctgaa acttaaagga attgacggaa gggcaccacc     1320
aggagtggag cctgcggctt aatttgactc aacacgggaa acctcacccg gcccggacac     1380
ggacaggatt gacagattga tagctctttc tcgattccgt gggtggtggt gcatggccgt     1440
tcttagttgg tggagcgatt tgtctggtta attccgataa cgaacgagac tctggcatgc     1500
taactagtta cgcgaccccc gagcggtcgg cgtcccccaa cttcttagag gacaagtgg      1560 cgttcagcca cccgagattg agcaataaca ggtctgtgat gcccttagat gtccggggct     1620
gcacgcgcgc tacactgact ggctcagcgt gtgcctaccc tacgccggca ggcgcgggta     1680
acccgttgaa ccccattcgt gatgggggatc ggggattgca attattcccc atgaacgagg    1740
aattcccagt aagtgcgggt cataagcttg cgttgattaa gtccctgccc tttgtacaca     1800
ccgcccgtcg ctactaccga ttggatggtt tagtgaggcc ctcggatcgg ccccgccggg    1860
gtcggcccac ggcctggcgg agcgctgaga agacggtcga acttgactat ctagaggaag    1920
taaaagtcgt aacaaggttt ccgtaggtga acctgcggaa ggatcatta                1969
```

<210> SEQ ID NO 12
<211> LENGTH: 23
<212> TYPE: DNA
<213> ORGANISM: Artificial Sequence
<220> FEATURE:
<223> OTHER INFORMATION: synthetic primer

<400> SEQUENCE: 12
agcaagattc agaccctcaa gct                                              23

<210> SEQ ID NO 13
<211> LENGTH: 25
<212> TYPE: DNA
<213> ORGANISM: Artificial Sequence
<220> FEATURE:
<223> OTHER INFORMATION: synthetic primer

```
<400> SEQUENCE: 13
cctggtagag gaagtcgatg tacct                                          25

<210> SEQ ID NO 14
<211> LENGTH: 19
<212> TYPE: DNA
<213> ORGANISM: Artificial Sequence
<220> FEATURE:
<223> OTHER INFORMATION: synthetic primer

<400> SEQUENCE: 14
tgtttgcaag atctgcggc                                                 19

<210> SEQ ID NO 15
<211> LENGTH: 20
<212> TYPE: DNA
<213> ORGANISM: Artificial Sequence
<220> FEATURE:
<223> OTHER INFORMATION: synthetic primer

<400> SEQUENCE: 15
tgcagtgagg gcaagaaaaa                                                20

<210> SEQ ID NO 16
<211> LENGTH: 20
<212> TYPE: DNA
<213> ORGANISM: Artificial Sequence
<220> FEATURE:
<223> OTHER INFORMATION: synthetic primer

<400> SEQUENCE: 16
gctacacgtt tgcctaccgc                                                20

<210> SEQ ID NO 17
<211> LENGTH: 21
<212> TYPE: DNA
<213> ORGANISM: Artificial Sequence
<220> FEATURE:
<223> OTHER INFORMATION: synthetic primer

<400> SEQUENCE: 17
cgattacctg ctccttgggt t                                              21

<210> SEQ ID NO 18
<211> LENGTH: 19
<212> TYPE: DNA
<213> ORGANISM: Artificial Sequence
<220> FEATURE:
<223> OTHER INFORMATION: synthetic primer

<400> SEQUENCE: 18
cttccagcag ccctacgac                                                 19

<210> SEQ ID NO 19
<211> LENGTH: 18
<212> TYPE: DNA
<213> ORGANISM: Artificial Sequence
<220> FEATURE:
<223> OTHER INFORMATION: synthetic primer

<400> SEQUENCE: 19
cggtggggtt gaggatct                                                  18

<210> SEQ ID NO 20
<211> LENGTH: 22
```

```
<212> TYPE: DNA
<213> ORGANISM: Artificial Sequence
<220> FEATURE:
<223> OTHER INFORMATION: synthetic primer

<400> SEQUENCE: 20
ggaactatga aaagtgggct tg                                              22

<210> SEQ ID NO 21
<211> LENGTH: 20
<212> TYPE: DNA
<213> ORGANISM: Artificial Sequence
<220> FEATURE:
<223> OTHER INFORMATION: synthetic primer

<400> SEQUENCE: 21
aaattgccag gctcaatgac                                                 20

<210> SEQ ID NO 22
<211> LENGTH: 21
<212> TYPE: DNA
<213> ORGANISM: Artificial Sequence
<220> FEATURE:
<223> OTHER INFORMATION: synthetic primer

<400> SEQUENCE: 22
gaaagtgatc cagccaaatg g                                               21

<210> SEQ ID NO 23
<211> LENGTH: 21
<212> TYPE: DNA
<213> ORGANISM: Artificial Sequence
<220> FEATURE:
<223> OTHER INFORMATION: synthetic primer

<400> SEQUENCE: 23
tgggcggtgt agaatcagag t                                               21

<210> SEQ ID NO 24
<211> LENGTH: 22
<212> TYPE: DNA
<213> ORGANISM: Artificial Sequence
<220> FEATURE:
<223> OTHER INFORMATION: synthetic primer

<400> SEQUENCE: 24
acactatcct gatgcttttg tg                                              22

<210> SEQ ID NO 25
<211> LENGTH: 19
<212> TYPE: DNA
<213> ORGANISM: Artificial Sequence
<220> FEATURE:
<223> OTHER INFORMATION: synthetic primer

<400> SEQUENCE: 25
gaacttggct cttcggttc                                                  19

<210> SEQ ID NO 26
<211> LENGTH: 22
<212> TYPE: DNA
<213> ORGANISM: Artificial Sequence
<220> FEATURE:
<223> OTHER INFORMATION: synthetic primer

<400> SEQUENCE: 26
```

```
ccttccgtaa ctggatgaac tc                                              22

<210> SEQ ID NO 27
<211> LENGTH: 22
<212> TYPE: DNA
<213> ORGANISM: Artificial Sequence
<220> FEATURE:
<223> OTHER INFORMATION: synthetic primer

<400> SEQUENCE: 27
ggatgcttcc ctaattcaac ag                                              22
```

DIFFERENT LEVELS IN BLOOD CELL SAMPLES OF EMT-MARKERS FOR THE DIAGNOSIS OF CANCER, IN PARTICULAR OF COLORECTAL (CRC) AND PANCREATIC (PC) CANCER

CROSS-REFERENCE TO RELATED APPLICATIONS

This application is a 371 of PCT/EP2014/078095, filed Dec. 16, 2014, which claims the benefit of European Patent Application No. EP13197367.9 filed Dec. 16, 2013.

FIELD OF THE INVENTION

The present invention refers to the field of molecular markers for disease diagnosis, preferably for cancer diagnosis. The present invention is aimed at detecting and measuring mRNA levels of genes involved in epithelial to mesenchymal transition in biological samples, i.e. in peripheral blood samples of tumor patients, to determine the presence of disease, its progression and risk of recurrence.

BACKGROUND

Circulating tumor cells (CTCs) are an heterogeneous population of cancer cells circulating in the peripheral blood that have been shed from either a primary tumor or its metastasis. Currently, the raw number and corresponding phenotype of CTCs in the whole blood of cancer patients has clinical relevance with respect to patient prognosis. CTC pool includes cells with epithelial, mesenchymal and stemness-like features. It has been shown that cancer intravasation in humans (Min Yu et al., *Science*, 2013, 339, 580) and animals is coupled with epithelial to mesenchymal transition (EMT), a process driven by transcription factors (TFs; like but not limited to TWIST1, ZEB1, ZEB2, SLUG, SNAIL, PRXX1, etc) and likely reversible (mesenchymal-to-epithelial transition, MET) at metastatic niches and ensuing in modification of cellular epithelial and/or mesenchymal markers (as e.g. CDH1 and Plastin 3). All said transcription factors/genes are involved in epithelial to mesenchymal transition (EMT-markers).

Therefore, the detection of EMT-markers in human blood is expected to provide diagnostic and prognostic dues.

Celesti et al. (*Gastroenterology* 2013, 145, 647) showed that levels of TWIST1 mRNA were statistically (median value) significantly higher in blood samples from patients with Colo-Rectal Cancer (CRC) than from controls. Unfortunately the distribution of TWIST1 levels in patients and controls partially overlaps, rendering the measurement of TWIST1 mRNA alone not reliable and suitable for diagnosis.

Hung Pham et al. (Pancreas 2010, 39, 3, 332-339) suggests that the overexpression of SLUG mRNA in pancreatic cancer tissue samples is correlated to the down regulation of PDGH, resulting in enhanced PGE2 production. However, the document doesn't teach that the measurement of SLUG mRNA alone in blood samples is reliable and suitable for diagnosis of pancreatic cancer.

DESCRIPTION OF THE INVENTION

Conventional, FDA-approved methods (i.e. Cell Search" (Veridex), "Adna Test Breast Cancer Select" and "Adna test Breast Cancer Detect" (AdnaGen AG), "Biocept Onco CEE" (Biocept Laboratories) detect epithelial antigens expressed, among others, by CTCs. Hence the diagnostic and prognostic value of these tests is limited.

The authors show quantitative RT-PCR assay specific for epithelial-mesenchymal transition (EMT) genes present in circulating cells of tumor patients. Differently from what reported by prior art no prior separation of circulating cell populations is needed prior to mRNA extraction. This approach allows detecting increased levels of circulating EMT-TF transcripts, irrespective of any antigenic or phenotypic cell feature.

Authors found that high levels of TWIST1, SLUG, and low levels of ZEB1 mRNAs are present in blood cells of CRC patients, whereas high levels of SLUG, TWIST 1 and ZEB2 mRNA are present in blood cells of pancreatic cancer (PC) patients, thus allowing a more reliable and robust diagnosis.

It is therefore an object of the present invention a method for determining if a subject is affected by a cancer comprising the step of assaying a blood cell sample from said subject for the presence of a panel of mRNAs comprising at least SLUG and TWIST1 mRNA wherein:

a) the increase of mRNA levels of both TWIST1 and SLUG genes but not of ZEB2 gene with respect to control samples is indicative of a colorectal cancer, b) the increase of mRNA levels of all of TWIST1, SLUG and ZEB2 genes with respect to control samples is indicative of a pancreatic cancer, c) the increase of at least SLUG mRNA level with respect to a first SLUG cut-off is indicative of colorectal or pancreatic cancer, d) in subjects wherein the SLUG mRNA level is not increased with respect to said first SLUG cut-off, the increase of TWIST1 mRNA level with respect to a TWIST1 cut-off is indicative of colorectal cancer, provided that said subject also shows an increase of SLUG mRNA with respect to a second SLUG cut off, said second SLUG cut-off being lower than the first SLUG cut off, and/or a decrease of CDH1 mRNA level with respect to a CDH1 cut-off, e) in subjects wherein the SLUG mRNA level is not increased, the increase of TWIST1 mRNA level with respect to a TWIST1 cut-off is indicative of pancreatic cancer, provided that said subject also shows an increase of ZEB2 mRNA level.

In the above method control samples are samples from normal subject or patients with different cancers respect to PC or CRC.

Preferably, in the method according to the invention the increase of both SLUG and TWIST1 mRNA levels with respect to respective cut-offs is indicative of colorectal or pancreatic cancer.

Preferably, in the method according to the invention, in subject wherein SLUG mRNA level is increased with respect to a first SLUG cut-off and TWIST1 mRNA level is not increased with respect to a TWIST1 cut-off, an increase of ZEB2 mRNA level with respect to a ZEB2 cut off is indicative of pancreatic cancer.

Preferably, in the method according to the invention, in subject wherein SLUG mRNA level is Increased with respect to a first SLUG cut-off and TWIST1 mRNA level is not increased with respect to a TWIST1 cut-off, a decrease of CDH1 mRNA level with respect to a CDH1 cut-off, is indicative of colorectal cancer.

Preferably, in the method according to the present invention relevant cut-offs are as follows:
first SLUG cut off for colorectal cancer 7.93018E-9,
second SLUG cut off for colorectal cancer 1.84E-10,
first SLUG cut off for pancreatic cancer 3.27E-9, TWIST1 cut off for colorectal cancer 1.00725E-8,
TWIST1 cut off for pancreatic cancer 1.35E-8,
CDH1 cut off: 7.29E-8,
ZEB2 cut off for pancreatic cancer 7.19E-6.

Another object of the invention is a method for discriminating between colorectal and pancreatic cancer among subjects that result to be positive to the above method comprising the step of assaying a blood cell sample from said subjects, wherein the increase of any one of ZEB1 and/or ZEB2 and/or CDH1 mRNAs with respect to a proper control from a patient with colorectal cancer is indicative of a pancreatic cancer.

Preferably, in the above method ZEB2 mRNA level is increased with respect to a cut off of 4.08E-5 and/or the CDH1 mRNA increased with respect to a cut off of 1.022E-7.

Another object of the invention is a method for determining the stage of a colorectal cancer in an affected subject comprising the step of assaying a blood cell sample from said subject wherein:

a) the increase of ZEB1 mRNA level with respect to control samples from subjects with colorectal cancer is indicative of a less advanced stage of colorectal cancer and/or b) the decrease of CDH1 mRNA levels with respect to control samples from subjects with colorectal cancer is indicative of metastatic (i.e. stage IV) disease at diagnosis, and/or c) the increase of TWIST1 mRNA levels with respect to control samples from subjects with colorectal cancer, is indicative of the development of a metachronous metastasis.

In the above method for determining the stage of a colorectal cancer in an affected subject, in the step a) a control sample may be a sample obtained from a subject known stage of colorectal cancer; In the step b) a control sample may be a sample obtained from a subject with colorectal cancer but without metastatic lesions; in the step c) a control sample may be a sample obtained from a subject with colorectal cancer who did not develop metastatic progression.

In the methods according to the invention said blood cell sample is preferably a Circulating Tumor Cell (CTC) enriched cell sample.

Preferably, said Circulating Tumor Cell (CTC) enriched cell sample is a Peripheral Blood Mononuclear Cell (PBMC) sample.

In the methods according to the invention the levels of mRNAs are preferably obtained by RT-PCR.

Any other method to detect specific mRNA in a blood sample known to the expert in the art are within the scope of the instant invention. Illustrative examples are: PCR amplification methods (QX200™ Droplet Digital™ PCR System, TaqMan Probes), other amplification methods; up to single cell gene expression analysis (miRGE—nCounter®).

The method of the invention is able to detect EMT transcripts in blood samples of humans or animals; in a particular aspect the method comprises the steps of:

a) Ficoll gradient density separation of Peripheral Blood Mononuclear Cells (PBMC), b) detection of the expression levels of EMT genes using RT-PCR, c) comparison of the level of the EMT genes from the patient to normal control levels, d) diagnosing the patient as having a specific tumor if the detected levels of the EMT genes are statistically significantly different (higher or lower than a predetermined cut off value depending on the selected gene) than the control level.

Another object of the invention is the use of a quantitative RT-PCR kit for working the methods as above described:
retrotranscribing means to get specific cDNAs;
specific amplification probes for amplifying specific cDNAs;
detecting means to detect and measure the level of amplified specific cDNAs.

Preferably said amplification probes are able to amplify:
the nt. 781-835 region of TWIST1, Acc. No.: NM_000474.3, (SEQ ID NO: 1);
the nt. 730-830 region of SLUG, Acc. No.: NM_003068.4, (SEQ ID NO: 2);
the nt. 1262-1361 region of ZEB2 Acc. No.: NM_014795.3, (SEQ IDNO: 3);
the nt. 4113-4172 region of CDH1, Acc. No.: NM_004360.3, (SEQ ID NO: 5);
the nt. 2917-3020 region of ZEB1, Acc. No.: NM_001128128.2, (SEQ IDNO: 6).

Preferably, said amplification probes have essentially the sequences:

```
TWIST1-Forward
                                    (SEQ ID NO: 12)
AGCAAGATTCAGACCCTCAAGCT;

TWIST1-Reverse
                                    (SEQ ID NO: 13)
CCTGGTAGAGGAAGTCGATGTACCT;

SLUG-Forward
                                    (SEQ ID NO: 14)
TGTTTGCAAGATCTGCGGC;

SLUG-Reverse
                                    (SEQ ID NO: 15)
TGCAGTGAGGGCAAGAAAAA;

ZEB2-Forward
                                    (SEQ ID NO: 16)
GCTACACGTTTGCCTACCGC;

ZEB2-Reverse
                                    (SEQ ID NO: 17)
CGATTACCTGCTCCTTGGGTT;

CDH1-Forward
                                    (SEQ ID NO: 20)
GGAACTATGAAAAGTGGGCTTG;

CDH1-Reverse
                                    (SEQ ID NO: 21)
AAATTGCCAGGCTCAATGAC;

ZEB1-Forward
                                    (SEQ ID NO: 22)
GAAAGTGATCCAGCCAAATGG;

ZEB1-Reverse
                                    (SEQ ID NO: 23)
TGGGCGGTGTAGAATCAGAGT.
```

DETAILED DESCRIPTION OF THE INVENTION

The invention shall be described with reference to non-limitative examples.

FIGURE LEGENDS

FIG. 1. mRNA levels of TWIST1 (A), SLUG (B), ZEB1 (C), in blood of 69 CRC patients as compared to 30 healthy controls.

Figure 2:
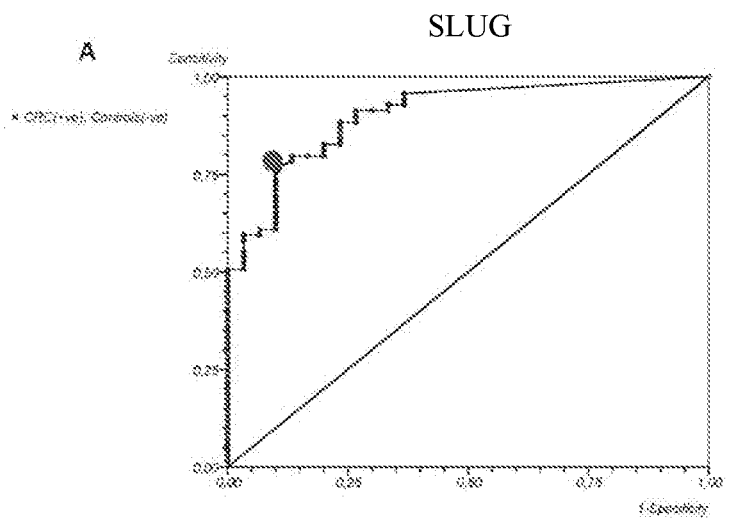
Figure 2:
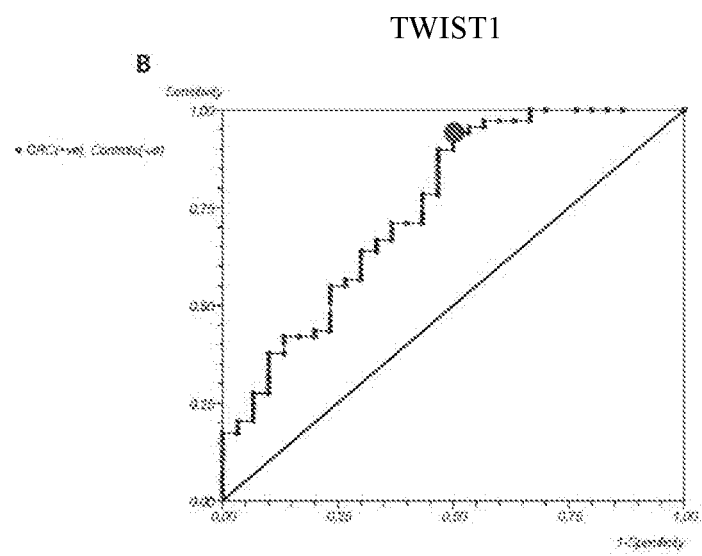

FIG. 2. ROC curves for SLUG (A), TWIST1 (B) mRNA levels in 69 patients with CRC as compared to 30 healthy controls.

Figure 3:
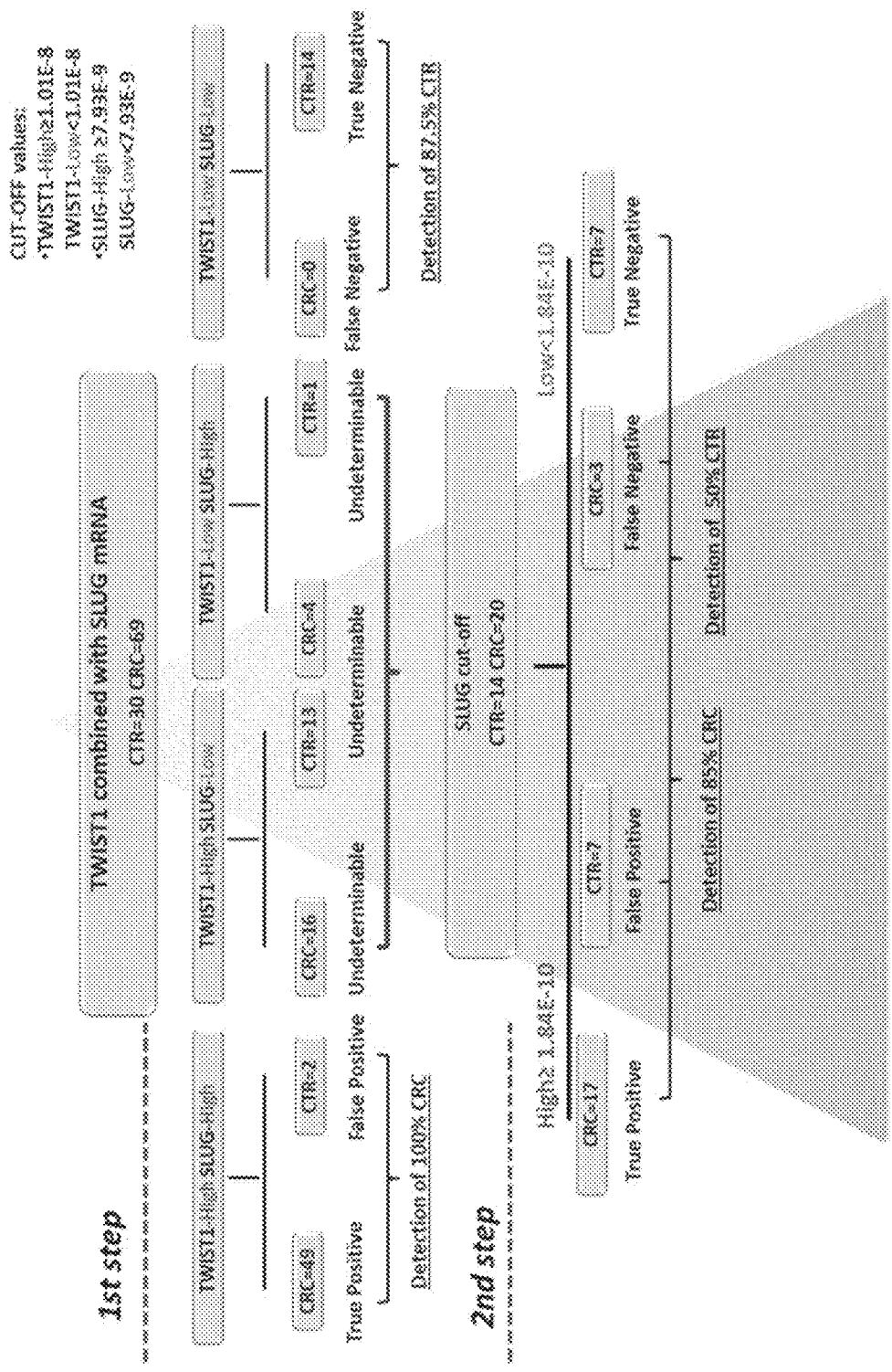

FIG. 3. Algorithm for diagnosis of CRC based upon the circulating levels of both TWIST1 and SLUG mRNAs (two-steps).

Figure 4:
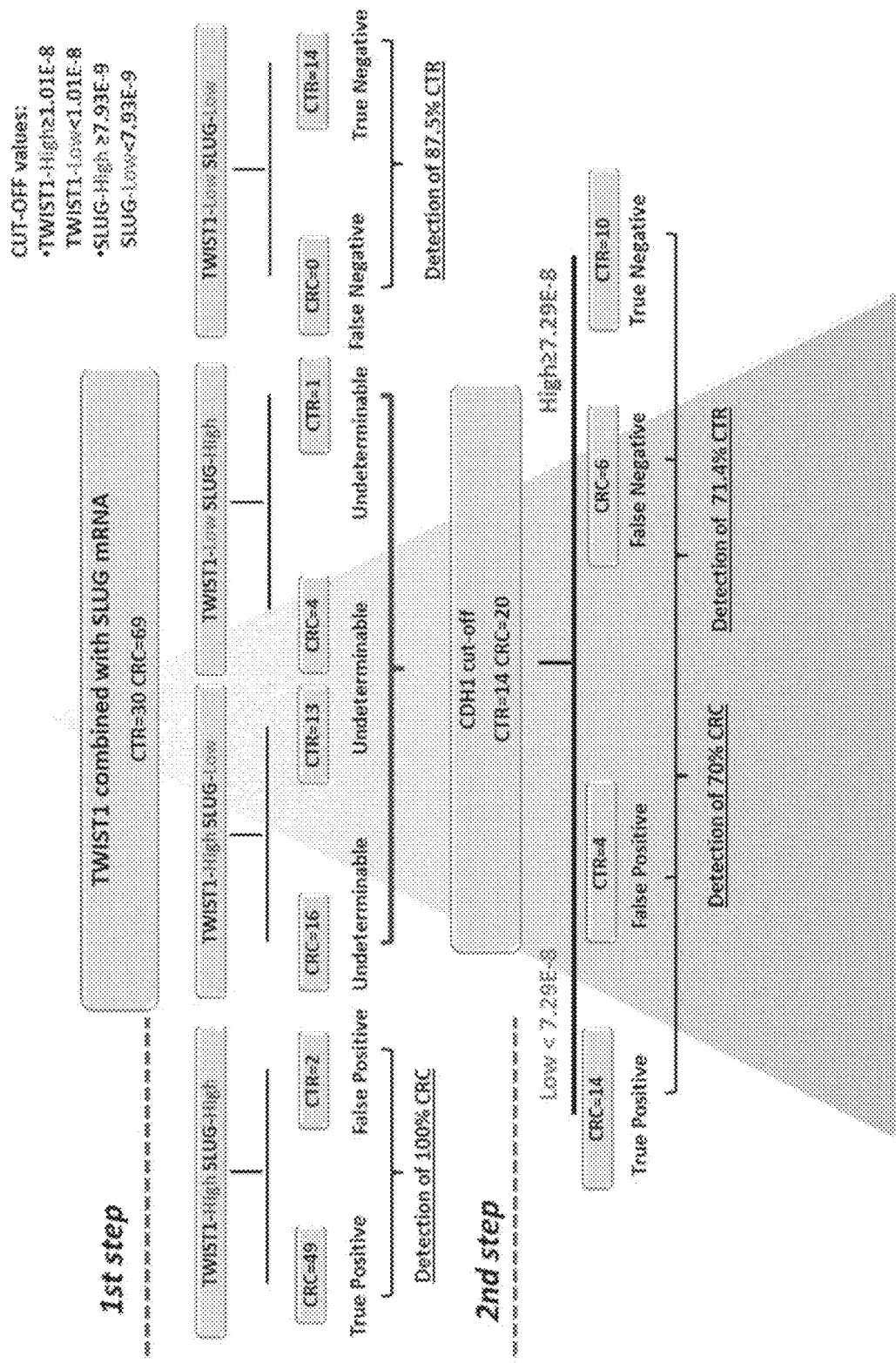

FIG. 4. Algorithm for diagnosis of CRC based upon the circulating levels of TWIST1-SLUG plus CDH1 mRNAs (two-steps).

Figure 5:
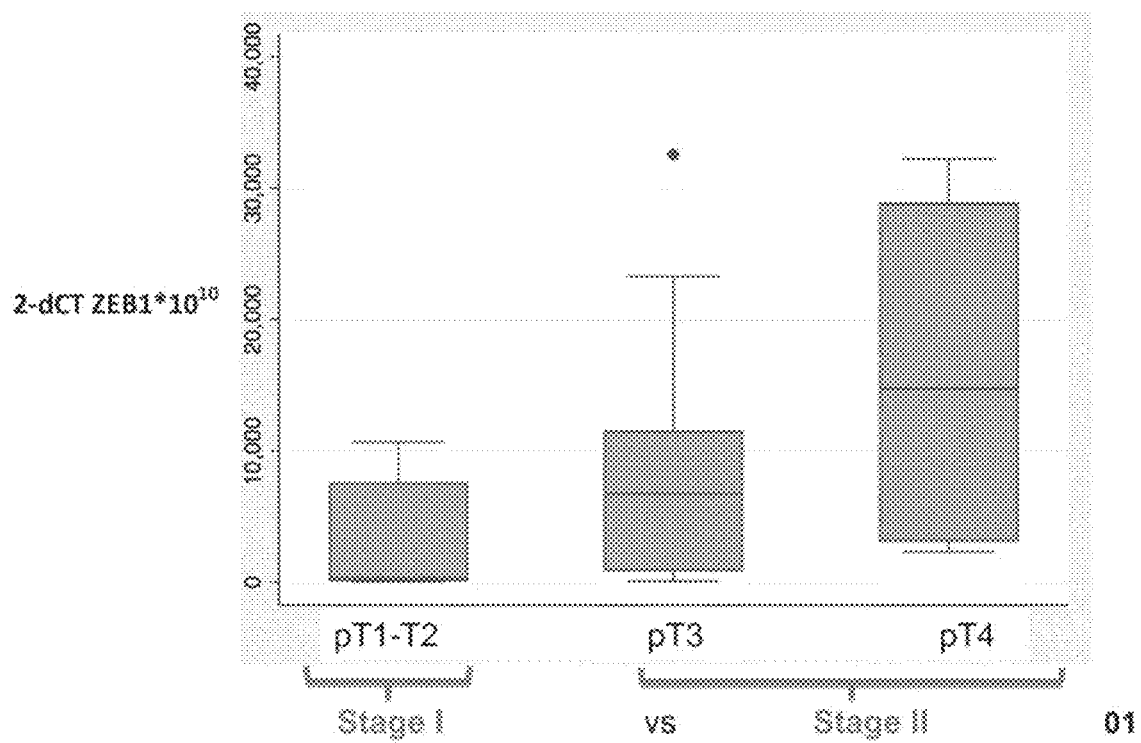

FIG. 5. Circulating mRNA levels of ZEB1 in patients with stage I and II CRC (pT1-4 N0).

Figure 6:
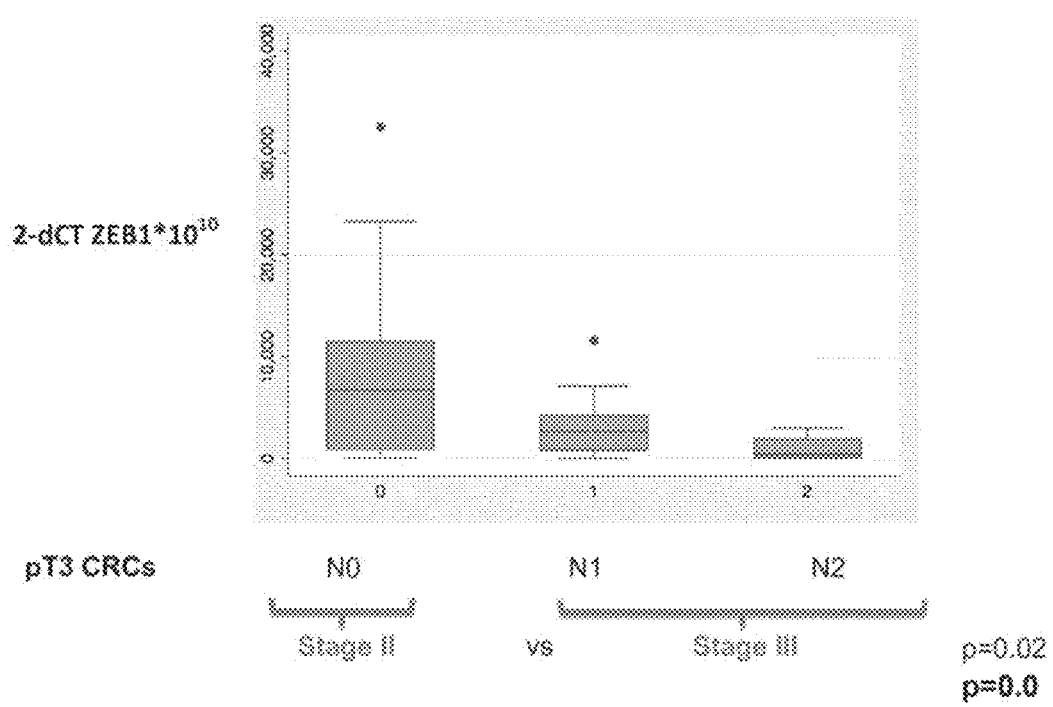

FIG. 6. Circulating mRNA levels of ZEB1 in patients with stage II (pT3 N0) and III (pT3 N1-2) CRC.

Figure 7:
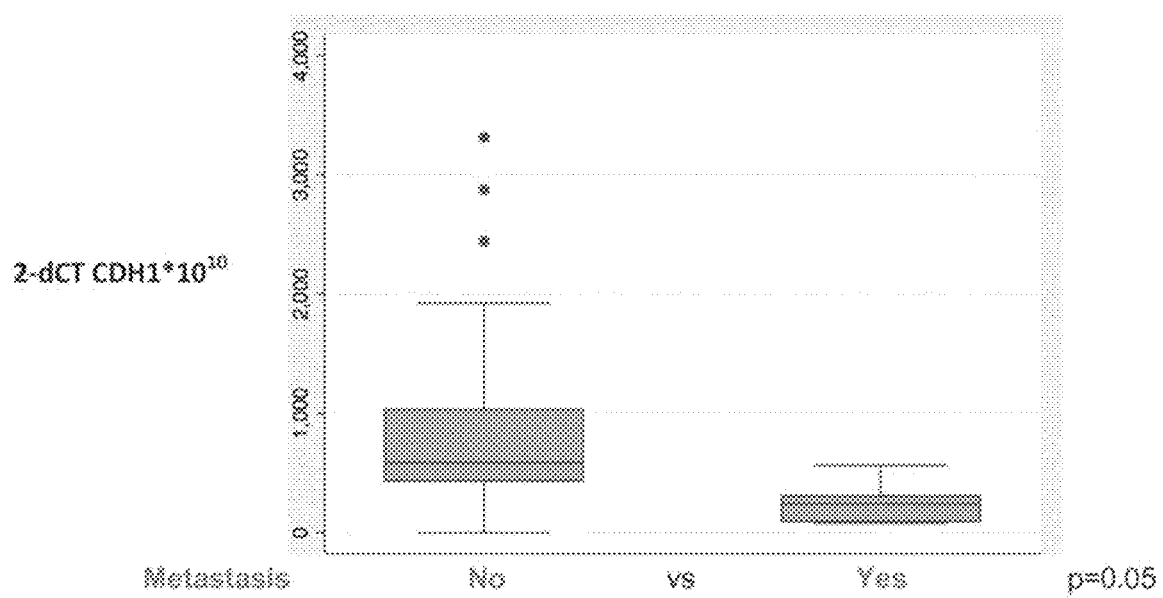

FIG. 7. Circulating mRNA levels of CDH1 in patients without (M0) and with (M+) metastatic disease at diagnosis.

Figure 8:
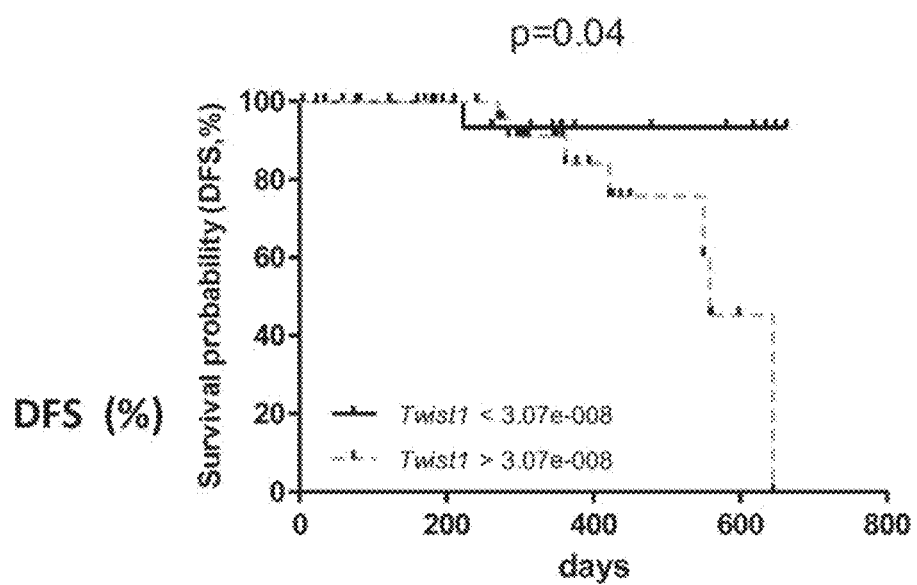

FIG. 8. High TWIST1 mRNA levels in circulating blood cells are associated with CRC metastatic progression (disease free survival—DFS—by Kaplan-Meier curves).

Figure 9:
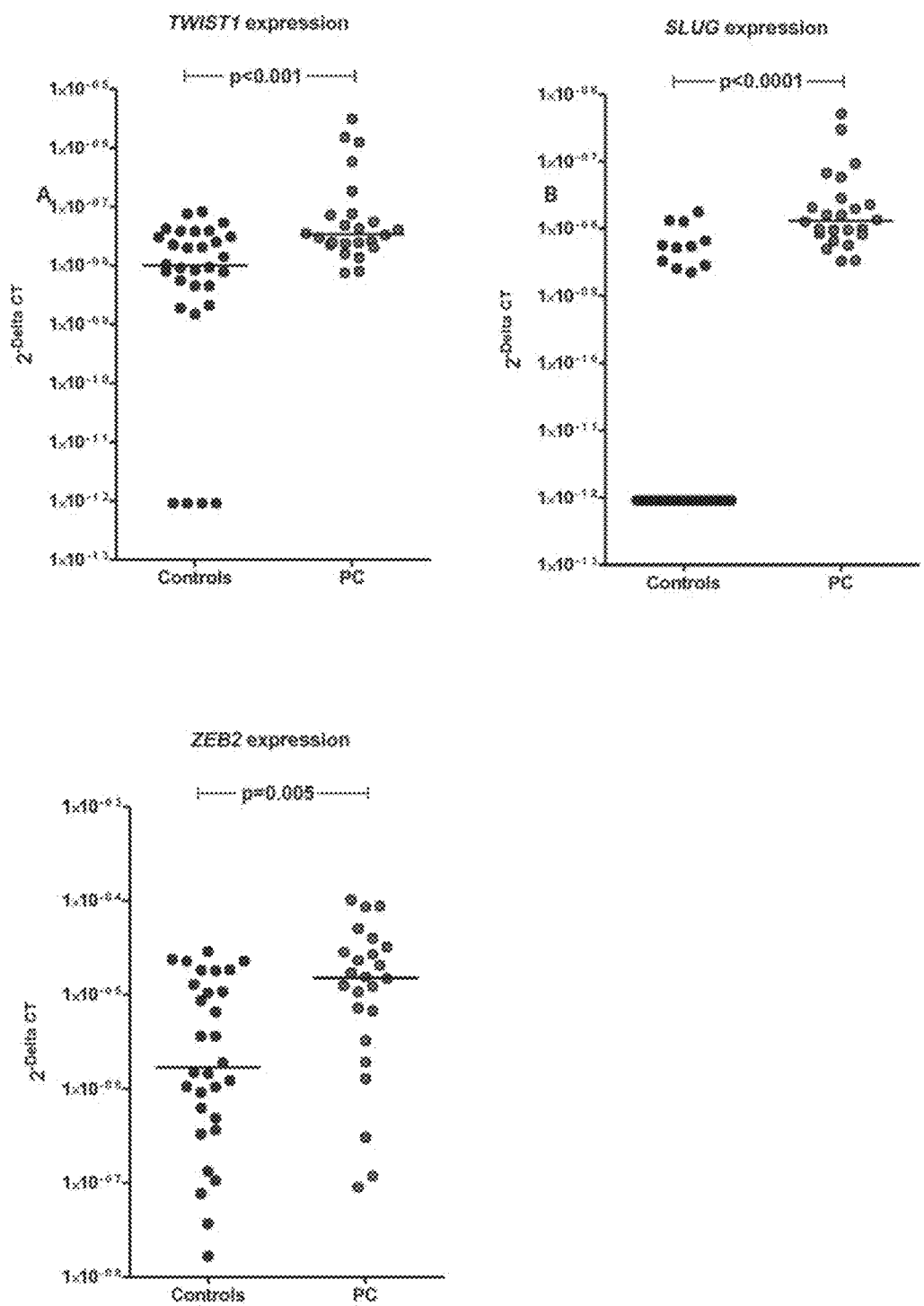

FIG. 9. TWIST1, SLUG and ZEB2 mRNA levels in the blood of PC patients and healthy controls.

Figure 10:
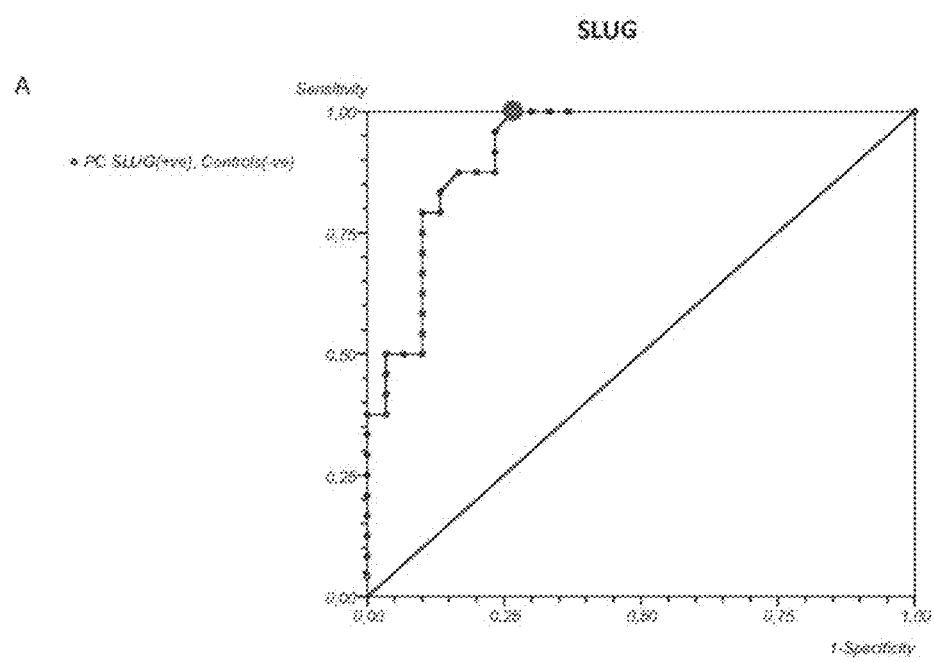

FIG. 10. ROC curve of SLUG mRNA levels discriminating PC patients (n=24) from healthy controls (n=30).

Figure 11:
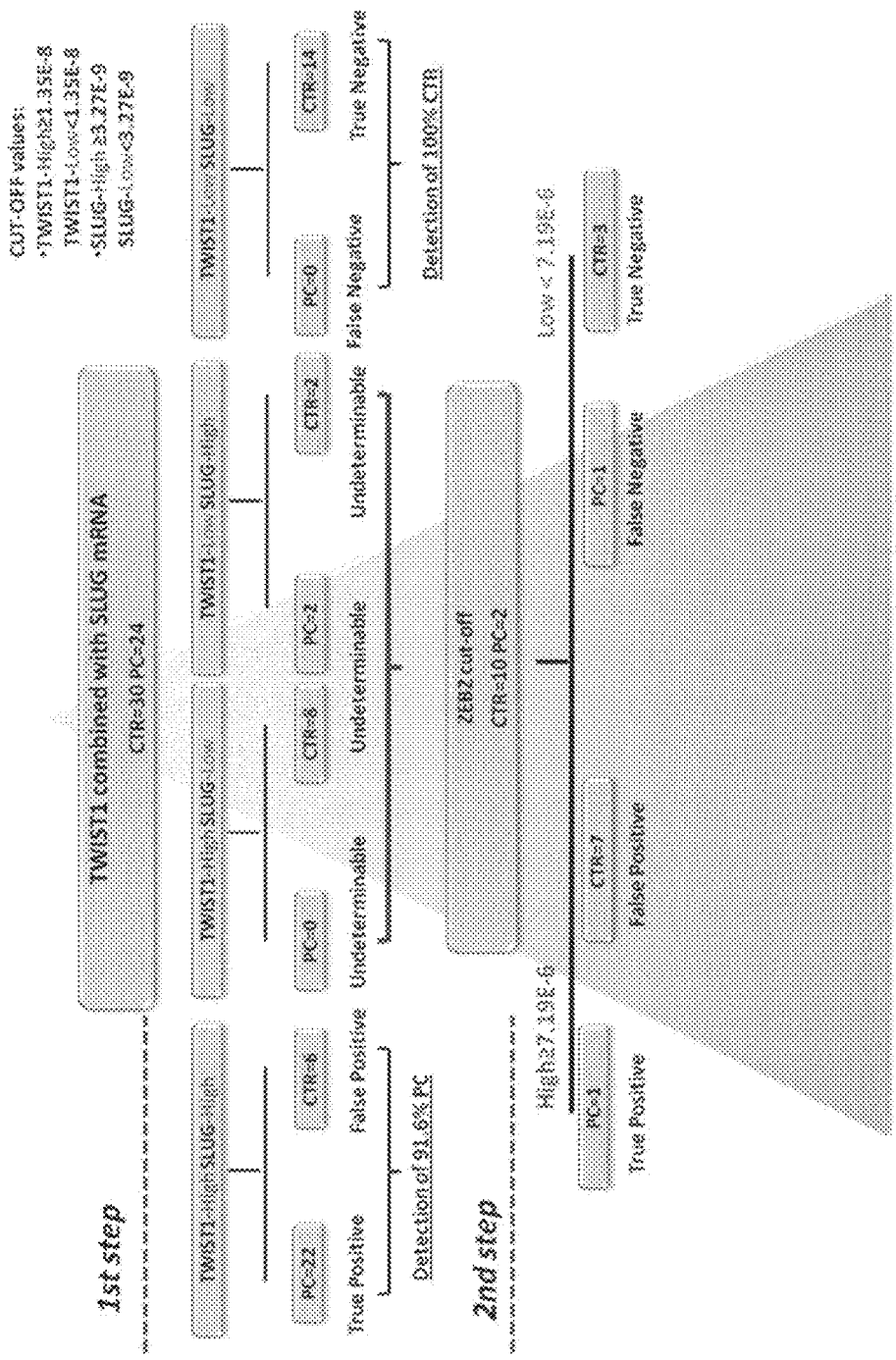

FIG. 11. Algorithm for diagnosis of PC based upon the circulating levels of TWIST1-SLUG plus ZEB2 mRNAs (two-steps).

Figure 12:
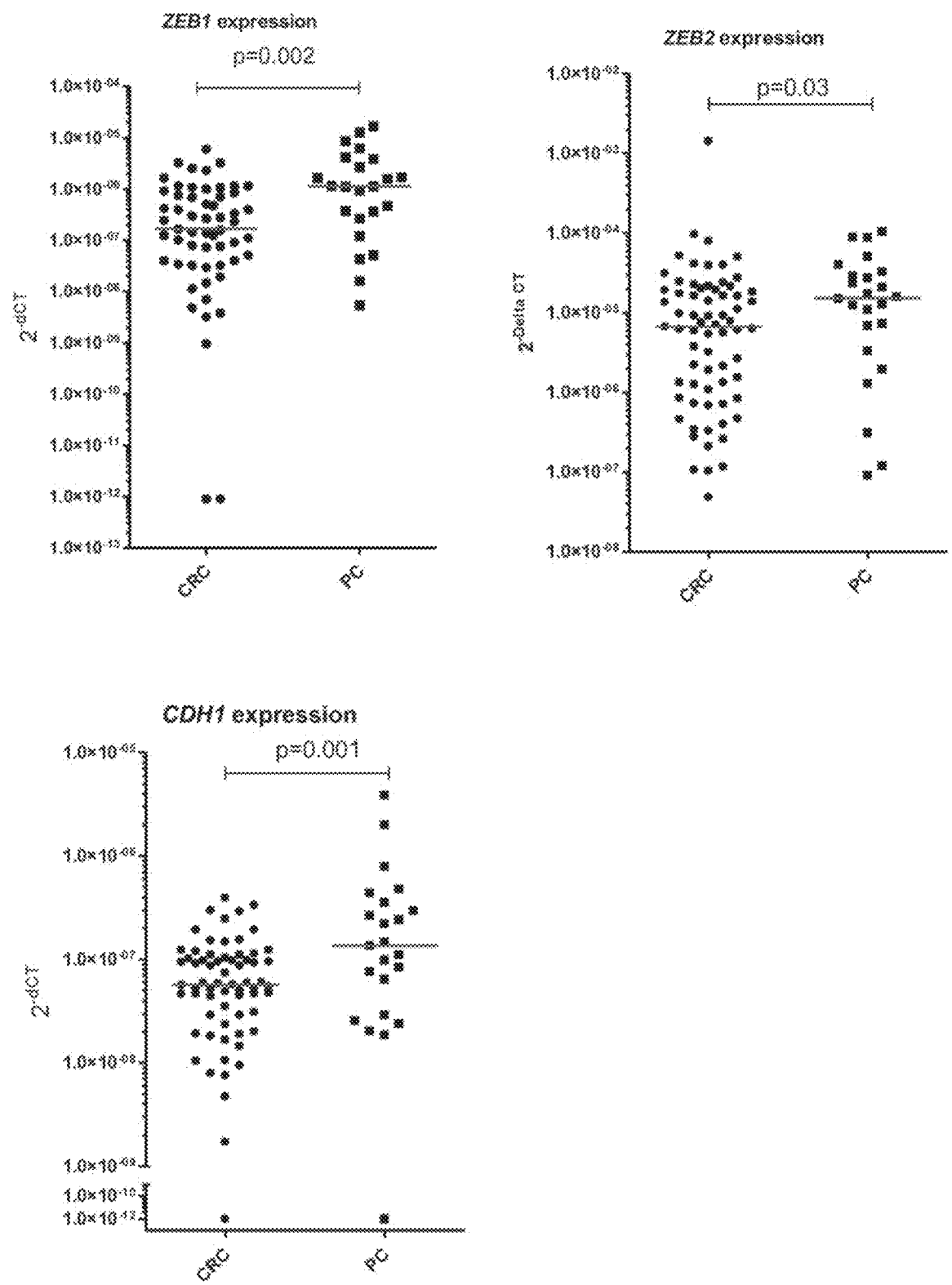

FIG. 12. Different circulating mRNA levels of ZEB1, ZEB2, and CDH1 in patients with PC and CRC.

MATERIALS AND METHODS

Quantification of Gene Transcripts in Unselected Blood Samples

Peripheral blood (6 mL) was collected in anticoagulants (EDTA, sodium citrate, heparin)-coated vacutainer and stored at 4° C. Peripheral blood was processed within 4 hours of collection and Ficoll-Paque Plus (GE Healthcare, Life Science) gradient separated according to the manufacturer's instructions. Briefly, 15 mL of Ficoll-Paque was added to a centrifuge tube and diluted PBS (6 mL+29 mL of balanced salt solution) was carefully layered on Ficoll-plaque. The unmixed solution was centrifuged (400 g for 40 minutes at 20° C.). Using a clean Pasteur pipette the upper layer was removed leaving untouched the lymphocyte layer at the interface. Next, by a new Pasteur pipette the PBMC layer (containing circulating tumor cells) was transferred to a dean centrifuge tube and washed with at least 3 volumes (18 ml) of balanced salt solution.

Once re-suspended, cells were centrifuged (300 g for 20 minutes at 20° C.), and the supernatant was then removed. After adding 50 mL of balanced salt solution cells pellet was finally centrifuged (200 g for 20 minutes at 20° C.). The supernatant was again removed and cells lysed with Qiagen lysis buffer plus β-Mercaptoethanol (1:100). Total RNA was then isolated using Qiagen Rneasy-Mini kit according to manufacturer's instructions. Thereafter, total RNA re-suspended in 60 μL of dethylphyrocarbonate-treated water (DEPC-water) was treated by DNAse (Ambion, Life Science) to minimize the contamination by genomic DNA.

All RNA preparation and handling steps took place in a laminar flow hood, under RNA-free conditions. RNA concentration was determined by absorbance reading at 260 nm using nanodrop.

Two μg of treated RNA were reverse transcribed to cDNA using High Capacity cDNA Reverse Transcription Kit (Applied Biosystem, Life Science). Synthesized cDNA was subjected to quantitative RT-PCR to detect and quantify EMT-gene mRNA levels:

TWIST1: NCBI Acc. No. NM_000474.3 (SEQ ID NO:1),
SLUG or SNAI2: NCBI Acc. No. NM_003068.4 (SEQ ID NO:2),
ZEB2 or SIP1: NCBI Acc. No. NM_014795.3 (SEQ ID NO:3),
SNAIL: NCBI Acc. No. NM_005985.3 (SEQ ID NO:4),
CDH1: NCBI Acc. No.: NM_004360.3 (SEQ ID NO: 5),
ZEB1: NCBI Acc. No.: NM_001128128.2 (SEQ ID NO: 6),
PRRX1: NCBI Acc. No.: NM_006902.4 (SEQ ID NO: 7),
PLASTIN3: NCBI Acc. No.: NM_005032.6 (SEQ ID NO: 8).

In brief, 1 μl of cDNA (40 ng) was placed in 20 μL of reaction volume containing 12 μl of Fast SyberGreen Master Mix, 3 μl of housekeeping and target Forward and Reverse Primers mixed at 5 μM and 4 μl of DEPC-water.

Specific primer sequences were:
18s-Forward CGC CGC TAG AGG TGA AAT TCT (SEQ ID NO: 9),
18s-Reverse CTT TCG CTC TGG TCC GTC TT (SEQ ID NO: 10);
to amplify the nt. 1049-1100 region of 18s, Acc. No.: M10098.1, NCBI, (SEQ ID NO: 11), as control;
TWIST1-Forward AGC AAG ATT CAG ACC CTC AAG CT (SEQ ID NO: 12);
TWIST1-Reverse CCT GGT AGA GGA AGT CGA TGT ACC T (SEQ ID NO: 13);
to amplify the nt. 781-835 region of TWIST1, Acc. No.: NM_000474.3, (SEQ ID NO: 1);
SLUG-Forward TGT TTG CAA GAT CTG CGG C (SEQ ID NO: 14);
SLUG-Reverse TGC AGT GAG GGC AAG AAA AA (SEQ ID NO: 15);
to amplify the nt. 730-830 region of SLUG. Acc. No.: NM_003068.4, (SEQ ID NO: 2);
ZEB2-Forward GCT ACA CGT TTG CCT ACC GC (SEQ ID NO: 16);
ZEB2-Reverse CGA TTA CCT GCT CCT TGG GTT (SEQ ID NO: 17);
to amplify the nt. 1262-1361 region of ZEB2 Acc. No.: NM_014795.3, (SEQ ID NO: 3);
SNAIL-Forward CTT CCA GCA GCC CTA CGA C, (SEQ ID NO: 18);
SNAIL Reverse CGG TGG GGT TGA GGA TCT (SEQ ID NO: 19);
to amplify the nt. 174-244 region of SNAIL, Acc. No.: NM_005985.3 (SEQ ID NO: 4).
CDH1-Forward GGAACTATGAAAAGTGGGCTTG (SEQ ID NO: 20);
CDH1-Reverse AAATTGCCAGGCTCAATGAC (SEQ ID NO: 21);
to amplify the nt. 4113-4172 region of CDH1, Acc. No.: NM_004360.3, (SEQ ID NO. 5);
ZEB1-Forward GAAAGTGATCCAGCCAAATGG (SEQ ID NO: 22);
ZEB1-Reverse TGGGCGGTGTAGAATCAGAGT (SEQ ID NO: 23);
to amplify the nt. 2917-3020 region of ZEB1, Acc. No.: NM_001128128.2, (SEQ ID NO: 6);
PRRX1-Forward ACACTATCCTGATGCTTT TGTG (SEQ IDNO: 24);
PRRX1-Reverse GAACTTGGCTCTTCGGTTC (SEQ ID NO: 25);
to amplify the nt. 395-494 region of PRRX1, Acc. No.: NM_006902.4 (SEQ ID NO: 7);
PLASTIN3-Forward CCTTCCGTAACTGGAT-GAACTC (SEQ ID NO: 26);

PLASTIN3-Reverse GGATGCTTCCCTAATTCAACAG (SEQ ID NO: 27)

to amplify the nt. 1624-1837 region of PLASTIN3, Acc. No.: NM_005032.6, (SEQ ID NO: 8).

Amplification was performed in an ABI 7900 HT Real Time PCR system (Applied Biosystem) using the program: 95*C for 10 minutes; 40 cycles of 95° C. for 15s and 60° C. for 60 s. All samples were analyzed in triplicate. Quantification of target genes and internal reference gene 18s was performed using the fluorescence emission of SyberGreen. DNA contamination was assessed by performing PCR on the no-reverse transcribed portion of each sample. For all samples fluorescence was detected after 0-40 cycles for the control and marker genes in a single reaction, which allow for the deduction of the cydes at threshold (CT) value for each product. The CT value was considered as the PCR cycle at which a significant increase in fluorescence is detected due to the exponential accumulation of double-strand PCR products. Expression of the target genes was normalized on the expression of the housekeeping gene, 18s to obtain the absolute quantification ($2^{-\Delta CT}$), while the relative quantification was calculated by $2^{\Delta\Delta CT}$ method to compare the transcript levels of controls versus patients (Livak Kj, Methods, 2001; 25(4):402-8).

Statistical Analysis

Mann-Whitney U-test was used to asses statistically significant differences in the expression levels of the circulating EMT-TF mRNAs between cancer patients and controls. For the EMT-TFs with significantly higher levels in CRC and Pancreatic cancer patients, sensitivity and specificity were estimated using the optimum cut-off points determined by ROC curves analysis. A p-value of <0.05 was deemed to be of statistical significance. All statistical analysis was conducted using StatDirect software (StatsDirect Ltd, Altrincham CHESHIRE, UK).

For each proposed diagnostic marker the following have been assessed:

Specificity (also called the true positive rate) measures the proportion of actual positives which are correctly identified as such. Specificity relates to the test's ability to exclude a condition correctly.

Sensitivity (also called the true negative rate) measures the proportion of negatives which are correctly identified as such. Sensitivity relates to the test's ability to identify a condition correctly.

The diagnostic odds ratio is a measure of the effectiveness of a diagnostic test. It is defined as the ratio of the odds of the test being positive if the subject has a disease relative to the odds of the test being positive if the subject does not have the disease.

The positive and negative predictive values (PPV and NPV respectively) are the proportions of positive and negative results in statistics and diagnostic tests that are true positive and true negative results.

The false positive rate is the expectancy of the false positive ratio, which refers to the probability of falsely rejecting the null hypothesis for a particular test The false negative rate is the rate of occurrence of negative test results in subjects known to have the disease or behavior for which an individual is being tested.

The False Omission Rate is the chance of not satisfying the null hypothesis among those that accept the null hypothesis The False discovery rate is the expected proportion of errors among the rejected hypotheses.

The positive likelihood ratio (LR+) defines how much increase the probability of disease if the test is positive the negative likelihood ratio (LR−) defines how much decrease the probability of disease if the test is negative The accuracy is the measure defining how close a test result comes to the true value.

Patients and Methods

The pilot study included 69 patients with CRC, and 24 patients with pancreatic cancer, plus 30 healthy control subjects. All samples were processed as above described after obtaining patient informed consent.

Results

1. High Levels of TWIST1, SLUG, and Low Levels of ZEB1 mRNAs are Present in Blood Cells of CRC Patients In healthy controls (n=30), coding mRNAs for ZEB1, ZEB2, CDH1, and SNAIL were detected in all samples (100%). TWIST1 and SLUG mRNAs were detected in 26 (87%) and 11 (36.7%) controls, respectively. Plastin3 mRNA was detected in 15 (50%), and PRRX1 mRNA in 4 (13%) samples.

In blood samples from 69 patients with CRC, authors detected TWIST1 (Fisher test vs controls p=0.007), ZEB2 and SNAIL mRNAs in all (100%) cases, and SLUG in 66 (95.7%; Fisher test vs controls p<0.001) cases. CDH1 was detectable in 65 out of 66 (98.5%) tested samples. In addition, in 57 tested samples, ZEB1 expression was detectable in 55 (96.5%), Plastin3 in 44 (77.2%), and PRRX1 in 3 (5.3%).

As Shown in FIG. 1, CRC patients had higher circulating levels of TWIST1 (FIG. 1A, absolute quantification, median, controls 9.93E-9 vs CRC 3.22 E-8; p<0.001) and SLUG (FIG. 1B, controls 9.09E-13 vs CRC, 1.83E-08; p<0.001) mRNAs. Conversely, ZEB1 levels were lower in CRC patients than in controls (FIG. 1C, controls 5.64E-7 vs CRC, 1.66E-07; p=0.02). The blood levels of ZEB2, SNAIL, CDH1, Plastin, PRRX1 mRNAs did not differ between cases and controls. Accordingly, as compared to controls, the levels of TWIST1 in blood cells of cancer patients were 2.3 times higher, those of SLUG 386 times higher, and those of ZEB1 5.1 times lower (relative quantification).

Threshold Values of TWIST1 and SLUG mRNAs in Blood Cells for Identifying CRC Patients.

Authors next determined the optimum cut-off point for high levels of transcripts discriminating CRC patients by ROC curve analysis (FIG. 2). By this approach, high levels of TWIST1 (above the cut-off, 1.01E-8) had 94.2% sensitivity and 50% specificity (Table 1 and FIG. 2B), and high SLUG levels (above the cut-off, 7.93E-9) had 76.8% sensitivity and 90% specificity in discriminating CRC patients from healthy controls (Table 2 and FIG. 2A).

TABLE 1

Diagnostic yields, sensitivity and specificity, for colorectal cancer of circulating levels of TWIST1 mRNA above the optimum cut-off values.

|  |  | Condition | | Prevalence | |
|---|---|---|---|---|---|
|  |  | Condition positive (CRC) | Condition Negative (CTR) | 69.7% | |
| Test outcome | Test outcome positive | 65 | 15 | PPV 0.81 | FDR 0.19 |
|  | Test outcome negative | 4 | 15 | FOR 0.210526316 | NPV 0.79 |
|  | LR+ 1.884057971 | TPR, Sensitivity 0.94 | FPR, Fall-out 0.500 | ACC 0.81 | |
|  | LR− 0.115942029 | FNR 0.058 | TNR, Specificity 0.5 | | |
|  | DOR 16.3 | | | | |

PPV = Positive Predictive Value
FDR = False discovery rate
FOR = False omission rate
NPV = Negative Predictive Value
ACC = Accuracy
TPR = True positive rate
FPR = False positive rate
FNR = False negative rate
TNR = True negative rate
LR+ = Positive likelihood ratio
LR− = Negative likelihood ratio
DOR = Diagnostic odds ratio

TABLE 2

Diagnostic yields, sensitivity and specificity, for colorectal cancer of circulating levels of SLUG mRNA above the optimum cut-off values.

|  |  | Condition | | Prevalence | |
|---|---|---|---|---|---|
|  |  | Condition positive (CRC) | Condition Negative (CTR) | 69.7% | |
| Test outcome | Test outcome positive | 53 | 3 | PPV 0.95 | FDR 0.05 |
|  | Test outcome negative | 16 | 27 | FOR 0.372093023 | NPV 0.63 |
|  | LR+ 7.68115942 | TPR, Sensitivity 0.768 | FPR, Fall-out 0.100 | ACC 0.81 | |
|  | LR− 0.257648953 | FNR 0.232 | TNR, Specificity 0.9 | | |
|  | DOR 29.8 | | | | |

PPV = Positive Predictive Value
FDR = False discovery rate
FOR = False omission rate
NPV = Negative Predictive Value
ACC = Accuracy
TPR = True positive rate
FPR = False positive rate
FNR = False negative rate
TNR = True negative rate
LR+ = Positive likelihood ratio
LR− = Negative likelihood ratio
DOR = Diagnostic odds ratio Combining Circulating Levels of TWIST1 and SLUG (with or without CDH1) mRNAs in Blood Cells for identifying PC Patients.

To discriminate CRC patients from healthy individuals we exploited TWIST1 sensitivity in conjunction with SLUG specificity. By means of this approach we first determined the specimens with high levels (i.e., above the cut-off) of both TWIST1 and SLUG mRNAs (CRC 49/69, 71%; controls 2/30, 6.6%) (FIG. 3). On the other side, low levels (i.e., below the cut-off) of both TWIST1 and SLUG mRNAs were detected only in controls (14/30, 33.3%). In the remaining samples (20 cases and 14 controls), 16 cases and 13 controls showed high-TWIST1-low-SLUG mRNA levels, and 4 cases and 1 control with low-TWIST1-high-SLUG mRNA levels. A second order SLUG ROC curve (cut-off 1.84E-10) was drawn for these 34 samples. According to the second order cut-off, 17 CRC samples showed high-SLUG levels and 3 low-SLUG levels, as compared to 7 controls with high-SLUG levels and 7 controls with low-SLUG levels. Eventually, the overall sensitivity and specificity of the two-steps TWIST1-SLUG algorithm were 95.7% and 70%, respectively. The positive and negative predictive values were 88% and 87.5%, respectively, with a diagnostic odds ratio of 51.3 (Table 3).

Alternatively, a second order CDH1 ROC curve (cut-off 7.29E-8) could be drawn for the 34 samples with high-TWIST1-low-SLUG and low-TWIST1-high-SLUG mRNA levels. According to the second order CDH1 cut-off, 14 CRC samples showed low-CDH1 levels and 6 high-CDH1 levels, as compared to 4 controls with low-CDH1 levels and 10 controls with high-CDH1 levels (FIG. 4). Accordingly, the alternative algorithm combining TWIST1 and SLUG plus CDH1 levels attained 91.3% overall sensitivity and 80% specificity. The positive and negative predictive values were 91% and 80%, respectively, with a diagnostic odds ratio of 42 (Table 4). The combination of two or more markers enhances the diagnostic performance of a single marker by matching substantially similar sensitivity with increased specificity, so that the rate of false positive tests is minimized in relationship to the rate of false negative ones, ensuing in improved diagnostic odds ratio and accuracy.

TABLE 3

Diagnostic yields, sensitivity and specificity, for colorectal cancer of circulating levels of TWIST1 and SLUG mRNAs above the optimum cut-off values, according to diagnostic algorithm 1.

|  |  | Condition | | Prevalence | |
|---|---|---|---|---|---|
|  |  | Condition positive (CRC) | Condition Negative (CTR) | 69.7% | |
| Test outcome | Test outcome positive | 66 | 9 | PPV 0.88 | FDR 0.12 |
|  | Test outcome negative | 3 | 21 | FOR 0.125 | NPV 0.88 |
|  | LR+ 3.19 | TPR, Sensitivity 0.957 | FPR, Fall-out 0.300 | ACC 0.88 | |
|  | LR− 0.062 | FNR 0.043 | TNR, Specificity 0.7 | | |
|  | DOR (DIAGNOSTIC ODDS RATIO) 51.3 | | | | |

PPV = Positive Predictive Value
FDR = False discovery rate
FOR = False omission rate
NPV = Negative Predictive Value
ACC = Accuracy
TPR = True positive rate
FPR = False positive rate
FNR = False negative rate
TNR = True negative rate
LR+ = Positive likelihood ratio
LR− = Negative likelihood ratio
DOR = Diagnostic odds ratio

TABLE 4

Diagnostic yields, sensitivity and specificity, for colorectal cancer of circulating levels of TWIST1, SLUG plus CDH1 mRNAs above the optimum cut-off values, according to diagnostic algorithm 2.

|  |  | Condition | | Prevalence | |
|---|---|---|---|---|---|
|  |  | Condition positive (CRC) | Condition Negative (CTR) | 69.7% | |
| Test outcome | Test outcome positive | 63 | 6 | PPV 0.91 | FDR 0.09 |
|  | Test outcome negative | 6 | 24 | FOR 0.2 | NPV 0.8 |
|  | LR+ 4.57 | TPR, Sensitivity 0.91 | FPR, Fall-out 0.20 | ACC 0.88 | |
|  | LR− 0.11 | FNR 0.09 | TNR, Specificity 0.80 | | |
|  | DOR 42 | | | | |

PPV = Positive Predictive Value
FDR = False discovery rate
FOR = False omission rate
NPV = Negative Predictive Value
ACC = Accuracy
TPR = True positive rate
FPR = False positive rate
FNR = False negative rate
TNR = True negative rate
LR+ = Positive likelihood ratio
LR− = Negative likelihood ratio
DOR = Diagnostic odds ratio Circulating Levels of ZEB1 and CDH1 mRNA in Blood Cells Differ According to TNM Features of Cancer at Diagnosis.

As to local invasion, the levels of ZEB1 mRNA were significantly lower in patients with pT1-T2 N0M0 (i.e., stage I) CRCs than in patients with pT3-T4 N0M0 (i.e., stage II) CRCs (Median, stage I 1.14E-7 vs stage II 4.51E-7, overall p=0.001) (FIG. 5). As to lymph-node metastasis, patients with CRC showing the same depth of local invasion (i.e. pT3) had higher circulating levels of ZEB1 mRNA levels in the absence of nodal invasion (i.e., N0) than when nodal invasion was present at pathological examination (N1-N2, Median, N0 6.72E-7 vs N1-2 2.66E-7; p=0.02) (FIG. 6). As to the presence of distant metastasis, patients with metastatic disease (M+) at diagnosis, displayed significantly lower circulating levels of CDH1 mRNA than those without metastatic lesions (M0; Median, M+2.38E-8 vs M0 5.88E-8, p=0.02) (FIG. 7).

Circulating levels of TWIST1 mRNA in blood cells discriminate progression to metastasis over time. In patients without distant CRC metastasis (stage I-III) at the time of diagnosis (n=54), circulating levels of TWIST1 mRNA were higher (>3.07E-8) in 7 out of 8 (87.5%) patients who later developed post-surgical metastatic progression. Accordingly, TWIST1 levels discriminated a significantly different disease free survival among patients with CRC (FIG. 8).

2. High Levels of TWIST1, SLUG, and ZEB2 mRNAs are Present in Blood Cells of Pancreatic Cancer (PC) Patients.

The levels of EMT-TF mRNA in the blood differ between PC patients and healthy individuals. As Shown in FIG. 9, compared to healthy controls, 24 PC patients had higher levels of TWIST1 (FIG. 9A, absolute quantification, median, controls 9.935E-9 vs PC 3.41E-8; p<0.001) and of SLUG (FIG. 9B, controls 9.09E-13 vs PC, 1.30E-8; p<0.0001), as well as of ZEB2 (FIG. 9C, controls 1.69E-6 vs PC 1.52E-5; p<0.01). Accordingly, the circulating levels of TWIST1, SLUG, and ZEB2 mRNAs in blood of PC patients were on average 14, 788, and 5 times higher, respectively, than in controls (relative quantification).

Threshold values of SLUG mRNA in blood identifying PC patients. By ROC curve analysis, high levels of SLUG (above the cut-off, 3.27E-9) by themselves reached 100% sensitivity and 70% specificity in discriminating cancer patients from healthy controls, reaching 75% positive and 100% negative predictive values, with a diagnostic odds ratio of 130 (FIG. 10 and Combining circulating levels of TWIST1 and SLUG with ZEB2 mRNAs in blood cells for identifying PC patients. To discriminate PC patients from healthy individuals we exploited TWIST1 in conjunction with SLUG. By means of this approach we first determined the specimens with high levels (i.e., above the cut-off) of both TWIST1 (cut-off, 1.35E-8) and SLUG mRNAs (PC 22/24, 91.6%; controls 6/30, 20%) (FIG. 11). On the other side, low levels (i.e., below the cut-off) of both TWIST1 and SLUG mRNAs were detected only in controls (14/30, 33.3%). In the remaining samples (2 cases and 10 controls), only 8 controls showed high-TWIST1-low-SLUG mRNA levels, and 2 cases and 2 controls with low-TWIST1-high-SLUG mRNA levels. A second order ZEB2 ROC curve (cut-off 7.19E-8) was drawn for these 12 samples. According to the second order cut-off, 1 PC sample showed high-ZEB2 levels and 1 low-ZEB2 level as compared to 7 controls with high-ZEB2 levels and 3 controls with low-ZEB2 levels. Eventually, the overall sensitivity and specificity of the two-step TWIST1-SLUG plus ZEB2 algorithm were 95.8% and 76.7%, respectively. The positive and negative predictive values were 76.7% and 95.8%, respectively, with a diagnostic odds ratio of 75.57 (Table 7).

ZEB1, ZEB2, and CDH1 mRNA levels are higher in blood cells of PC patients than in those of CRC patients. In addition, comparing EMT-gene levels in blood between PC and CRC patients, we found that the levels of ZEB1 (PC 1.14E-6 vs CRC 1.66E-7, p=0.002), ZEB2 (PC 1.52 E-5 vs CRC 6.62 E-6, p=0.03) and CDH1 (PC 1.36E-7 vs CRC 5.73E-8, p=0.001) were significantly higher in patients with PC than patients with CRC. By relative quantification, the transcript levels of ZEB1 were on average 7 times higher in PC than in CRC patients, while ZEB2 and CDH1 were both 2 times higher in PC than in CRC patients (FIG. 12).

Threshold values of CDH1 and ZEB2 mRNA levels in blood cells discriminating pancreatic from colorectal cancer. The cut-off value of CDH1 discriminating patients with pancreatic from those with colorectal cancer was 1.022E-7 yielding 75.4% specificity for pancreatic cancer (17 positive colorectal cancer positive out of 69) and sensitivity 58.3% (detecting 14 out of 24 pancreatic cancer patients). Subsequently, a second order ZEB2 cut-off (4.08E-5) allowed discriminating 5 out of 17 patients with colorectal cancer (ZEB2 values<4.08E-5) who were not detected by mean of CDH1 levels, while detecting 2 out of 10 patients with pancreatic cancer (ZEB2 values>4.08E-5) who were not detected by mean of CDH1 levels. Overall, combined use of CDH1 and ZEB2 mRNA levels led to discriminate patients with pancreatic cancer from those having colorectal cancer with 82% specificity and 66.7 sensitivity.

TABLE 5

Diagnostic yields, sensitivity and specificity for pancreatic cancer of circulating levels of SLUG mRNA above the optimum cut-off value.

| | | Condition positive (PC) | Condition Negative (CTR) | Prevalence 44.4% | |
|---|---|---|---|---|---|
| Test outcome | Test outcome positive | 24 | 8 | PPV 0.75 | FDR 0.25 |
| | Test outcome negative | 0 | 22 | FOR 0 | NPV 1 |
| | LR+ 3.75 | TPR, Sensitivity 1.000 | FPR, Fall-out 0.267 | ACC 0.85 | |

TABLE 5-continued

Diagnostic yields, sensitivity and specificity for pancreatic cancer of circulating levels of SLUG mRNA above the optimum cut-off value.

| | Condition positive (PC) | Condition Negative (CTR) | Prevalence 44.4% |
|---|---|---|---|
| LR− 0 | FNR 0.000 | TNR, Specificity 0.7 | |
| DOR 129.7 129 | | | |

PPV = Positive Predictive Value
FDR = False discovery rate
FOR = False omission rate
NPV = Negative Predictive Value
ACC = Accuracy
TPR = True positive rate
FPR = False positive rate
FNR = False negative rate
TNR = True negative rate
LR+ = Positive likelihood ratio
LR− = Negative likelihood ratio
DOR = Diagnostic odds ratio

TABLE 6

Diagnostic yields, sensitivity and specificity for pancreatic cancer of circulating levels of TWIST1 mRNA above the cut-off values.

| | | Condition | | Prevalence |
|---|---|---|---|---|
| | | Condition positive (PC) | Condition Negative (CTR) | 44.4% |
| Test outcome | Test outcome positive | 22 | 14 | PPV 0.61 | FDR 0.39 |
| | Test outcome negative | 2 | 16 | FOR 0.11 | NPV 0.89 |
| | LR+ 1.964285714 | TPR, Sensitivity 0.917 | FPR, Fall-out 0.467 | ACC 0.70 | |
| | LR− 0.15625 | FNR 0.083 | TNR, Specificity 0.533 | | |
| | DOR 12.57 | | | | |

TABLE 7

Diagnostic yields, sensitivity and specificity for pancreatic cancer of circulating levels of SLUG, TWIST1 and ZEB2 mRNA above the cut-off values.

| | | Condition | | Prevalence |
|---|---|---|---|---|
| | | Condition positive (PC) | Condition Negative (CTR) | 44.4% |
| Test outcome | Test outcome positive | 23 | 7 | PPV 0.77 | FDR 0.23 |
| | Test outcome negative | 1 | 23 | FOR 0.041666667 | NPV 0.958333 |
| | LR+ 4.107142857 | TPR, Sensitivity 0.958 | FPR, Fall-out 0.233 | ACC 0.85 | |

TABLE 7-continued

Diagnostic yields, sensitivity and specificity for pancreatic cancer of circulating levels of SLUG, TWIST1 and ZEB2 mRNA above the cut-off values.

| | Condition | Prevalence |
|---|---|---|
| | Condition positive (PC) Condition Negative (CTR) | 44.4% |
| LR− 0.054347826 | FNR 0.042 | TNR, Specificity 0.767 |
| DOR 75.57 | | |

PPV = Positive Predictive Value
FDR = False discovery rate
FOR = False omission rate
NPV = Negative Predictive Value
ACC = Accuracy
TPR = True positive rate
FPR = False positive rate
FNR = False negative rate
TNR = True negative rate
LR+ = Positive likelihood ratio
LR− = Negative likelihood ratio
DOR = Diagnostic odds ratio

The invention claimed is:

1. A method for determining the presence or absence of a colorectal or a pancreatic cancer in a subject, the method comprising:
   i) obtaining a peripheral blood sample from the subject,
   ii) measuring a panel of mRNAs comprising TWIST1, SLUG and ZEB2 genes in peripheral blood mononuclear cells (PBMC) isolated from the peripheral blood sample, and
   iii) identifying the subject having a colorectal or a pancreatic cancer wherein:
      a) when the mRNA levels of both TWIST1 and SLUG genes, but not of a ZEB2 gene, are increased in the subject with respect to control samples, the subject is identified as having colorectal cancer,
      b) when the SLUG mRNA level is increased in the subject with respect to a first SLUG cut-off, the subject is identified as having colorectal cancer,
      c) when the SLUG mRNA is not increased with respect to control samples, the ZEB2 mRNA is increased with respect to control samples and the TWIST1 mRNA is increased with respect to a TWIST1 cut-off in the subject, the subject is identified as having pancreatic cancer,
      d) when both SLUG and TWIST1 mRNA levels are increased with respect to respective cut-offs, the subject is identified as having colorectal cancer, or
      e) when TWIST1, SLUG and ZEB2 mRNA levels are all increased with respect to control samples, the subject is identified as having pancreatic cancer,
   wherein said cut-offs are determined by Receiver-Operator-Characteristic (ROC) curve analysis; and
   wherein said measuring uses a quantitative RT-PCR kit and comprises the steps of:
      isolating PBMC from the peripheral blood sample, extracting total mRNA;
      retrotranscribing the panel of mRNAs comprising TWIST1, SLUG and ZEB2 genes to get specific cDNAs;
      employing specific amplification primers for amplifying specific cDNAs; and
      detecting the level of amplified specific cDNAs;
   wherein said specific amplification primers comprise the sequence pairs, respectively:

```
         TWIST1-Forward
                                        (SEQ ID NO: 12)
         AGCAAGATTCAGACCCTCAAGCT;

TWIST1-Reverse
                                        (SEQ ID NO: 13)
         CCTGGTAGAGGAAGTCGATGTACCT;

SLUG-Forward
                                        (SEQ ID NO: 14)
         TGTTTGCAAGATCTGCGGC;

SLUG-Reverse
                                        (SEQ ID NO: 15)
         TGCAGTGAGGGCAAGAAAAA;

ZEB2-Forward
                                        (SEQ ID NO: 16)
         GCTACACGTTTGCCTACCGC; and ZEB2-Reverse
                                        (SEQ ID NO: 17)
         CGATTACCTGCTCCTTGGGTT.
```

2. The method according to claim 1, wherein said amplification primers are able to amplify the following regions:
   nucleotides 781-835 of TWIST1, Acc. No.: NM 000474.3, (SEQ ID NO: 1);
   nucleotides 730-830 of SLUG, Acc. No.: NM 003068.4, (SEQ ID NO: 2); and
   nucleotides 1262-1361 of ZEB2 Acc. No.: NM 014795.3, (SEQ ID NO: 3).

3. The method according to claim 1, wherein the measuring does not require removal of a population of circulating tumor cells before mRNA extraction.

4. A method for determining the stage of a colorectal cancer in a subject identified as having colorectal cancer by the method according to claim 1, further comprising assaying a peripheral blood sample from said subject for a ZEB1 mRNA level, a CDH1 mRNA level, and a TWIST1 mRNA level by reverse transcription PCR, employing further amplification primers, wherein:
   a) an increase of the ZEB1 mRNA level with respect to control samples from subjects with colorectal cancer is indicative of a less advanced stage of colorectal cancer and/or
   b) a decrease of the CDH1 mRNA level with respect to control samples from subjects with colorectal cancer is indicative of metastatic disease at diagnosis, and/or
   c) an increase of the TWIST1 mRNA level with respect to control samples from subjects with colorectal cancer, is indicative of the development of a metachronous metastasis;
wherein said further amplification primers are ZEB1 and CDH1 amplification primers that comprise the sequence pairs, respectively:
   CDH1-Forward    GGAACTATGAAAAGTGGGCTTG (SEQ ID NO: 20);

CDH1-Reverse AAATTGCCAGGCTCAATGAC (SEQ ID NO: 21);
ZEB1-Forward GAAAGTGATCCAGCCAAATGG (SEQ ID NO: 22); and
ZEB1-Reverse TGGGCGGTGTAGAATCAGAGT (SEQ ID NO: 23).

5. The method according to claim 4, wherein said ZEB1 and CDH1 amplification primers are able to amplify the following respective regions:
nucleotides 4113-4172 of CDH1, Acc. No.: NM_004360.3, (SEQ ID NO: 5); and
nucleotides 2917-3020 of ZEB1, Acc. No.: NM_001128128.2, (SEQ ID NO: 6).

* * * * *